United States Patent [19]

Begemann et al.

[11] Patent Number: 5,247,930
[45] Date of Patent: Sep. 28, 1993

[54] DUAL CHAMBER PACING SYSTEM WITH DYNAMIC PHYSIOLOGICAL TRACKING AND METHOD OF TIMING DELIVERED STIMULUS FOR OPTIMIZED SYNCHRONOUS PACING

[75] Inventors: Malcolm J. S. Begemann, Velp; Gustaaf A. P. Stoop, Dieren; Johannes S. van der Veen, Arnhem, all of Netherlands

[73] Assignee: Vitatron Medical, B.V., Netherlands

[21] Appl. No.: 831,115

[22] Filed: Feb. 4, 1992

[51] Int. Cl.$^5$ ............................................. A61A 1/362
[52] U.S. Cl. ...................................................... 607/11
[58] Field of Search .................... 128/419 PG, 419 PT

[56] References Cited

U.S. PATENT DOCUMENTS

| | | | |
|---|---|---|---|
| 4,429,697 | 2/1984 | Nappholz et al. | 128/419 PG |
| 4,432,362 | 2/1984 | Leckrone et al. | 128/419 PG |
| 4,452,248 | 6/1984 | Keller, Jr. | 128/419 PG |
| 4,503,857 | 3/1985 | Boute et al. | 128/419 |
| 4,527,568 | 7/1985 | Rickards | 128/419 PG |
| 4,539,991 | 9/1985 | Boute et al. | 128/419 |
| 4,554,921 | 11/1985 | Boute et al. | 128/419 |
| 4,577,634 | 3/1986 | Gessman | 128/419 PG |
| 4,624,260 | 11/1986 | Baker, Jr. et al. | 128/419 |
| 4,686,989 | 8/1987 | Smyth et al. | 128/419 PG |
| 4,712,554 | 12/1987 | Garson, Jr. | 128/419 PG |
| 4,712,556 | 12/1987 | Baker, Jr. | 128/419 |
| 4,714,079 | 12/1987 | Hedberg et al. | 128/419 |
| 4,722,341 | 2/1988 | Hedberg et al. | 128/419 PG |
| 4,872,459 | 10/1989 | Pless et al. | 128/419 PG |
| 4,920,965 | 5/1990 | Funke et al. | 128/419 |
| 4,932,406 | 6/1990 | Berkovits | 128/419 |
| 4,945,909 | 8/1990 | Fearnot et al. | 128/419 |
| 4,951,667 | 8/1990 | Markowitz et al. | 128/419 |
| 4,966,146 | 10/1990 | Webb et al. | 128/419 |
| 4,972,834 | 11/1990 | Begemann et al. | 128/419 |
| 5,027,815 | 7/1991 | Funke et al. | 128/419 PG |
| 5,123,412 | 6/1992 | Betzold | 128/419 PG |

OTHER PUBLICATIONS

Herz-schrittmacher, "Frequenzdynamische Stimulation-salgorithmen als Erganzung zum DDD-Schrittmacher," H. D. Funke, *Journal of Cardiac Pacing and Electrophysiology* 9:16-23 (1989).

"Rate Responsive Dual Chamber Pacing," Lukas J. Kappenberger and Loek Herpers, *Pace*, voo. 9, Nov.–Dec. 1986 Part II, pp. 987–991.

"Rate Responsive Dual Chamber Pacing," J. J. Goy et al., *Progress in Clinical Pacing*, 1986, pp. 60–65.

*Primary Examiner*—William E. Kamm
*Attorney, Agent, or Firm*—Woodcock Washburn Kurtz Mackiewicz & Norris

[57] ABSTRACT

A dual chamber pacemaker system is provided having means for determining when sensed atrial signals have a physiological rate, and tracking only such sensed atrial signals as are found to have physiological rates. The pacemaker provides logic means for continuously determining a physiological rate as a function of sensed atrial rate, whereby physiological rate substantially tracks the rate of sensed physiological atrial signals. The pacemaker also determines dynamic decision rates which are coupled to follow the physiological rate. The decision rates comprise a dynamic pacing limit, which sets the pacing escape interval; a dynamic tracking limit, which sets the upper limit of the physiological range of rates which are tracked; and the dynamic Wenckebach limit, which defines the upper rate for a dynamic Wenckebach range. The pacemaker enables time out of an AV delay for synchronizing delivery of ventricular pacing pulses with respect to atrial heartbeats which occur within the range between the dynamic pacing limit and the dynamic tracking limit, i.e., the physiological range. Synchronized ventricular pacing pulses are delivered when both the sensed atrial signal and the scheduled synchronized ventricular signal have rates within the determined physiological range. The pacemaker substantially continuously determines atrial rate, sensing all atrial signals except for a short PVAB which limits atrial sensing only to the extent required to block far field R-waves.

58 Claims, 18 Drawing Sheets

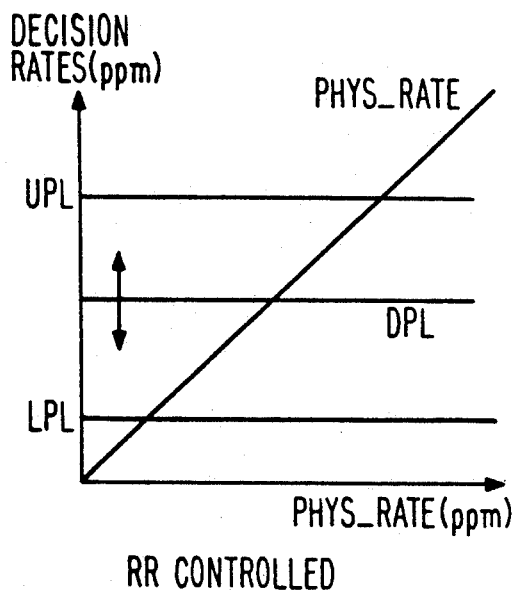
Fig. 5a RR CONTROLLED
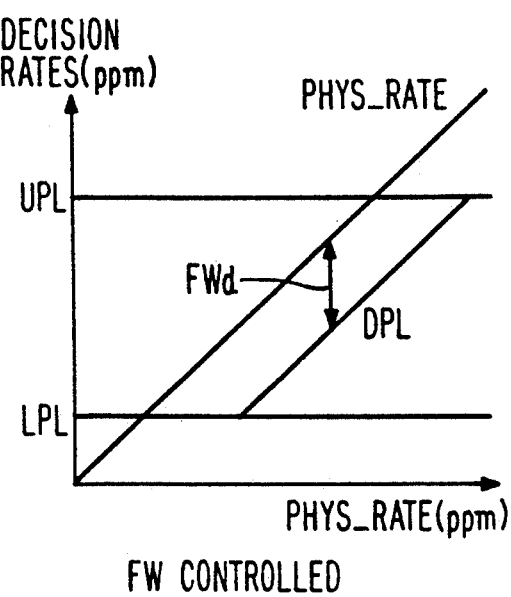
Fig. 5b FW CONTROLLED
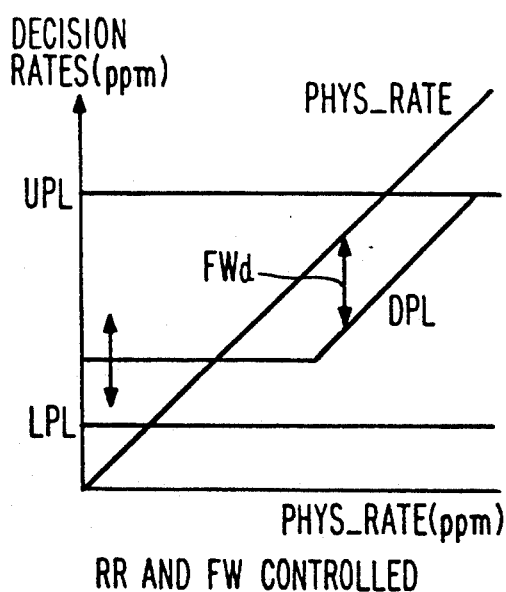
Fig. 5c RR AND FW CONTROLLED

INTERNAL TIMING:

INTERNAL TIMING:

INTERNAL TIMING:

INTERNAL TIMING:

DUAL CHAMBER PACING SYSTEM WITH DYNAMIC PHYSIOLOGICAL TRACKING AND METHOD OF TIMING DELIVERED STIMULUS FOR OPTIMIZED SYNCHRONOUS PACING

BACKGROUND OF THE INVENTION

1. Field of the Invention

This invention relates to cardiac pacing systems and, more particularly, to dual chamber pacing systems designed to operate in a synchronous tracking mode but which control the circumstances under which a ventricular stimulus is synchronously delivered following a sensed atrial heartbeat.

2. Description of the Prior Art

The advantages of dual chamber pacing, and more particularly pacing in different modes which are selected in response to different patient conditions, is now well recognized in the art. Early pacing systems were solely ventricular, and were sufficient for management of patient with complete heart block and Stokes-Adams attacks. However, ventricular demand pacemakers are not equipped to take advantage of atrial activity, and thus are limited in their efficiency. Subsequently, atrial synchronous, ventricular pacemakers were introduced, having a lead for sensing P signals from the atrium and another for pacing the ventricle after a suitable P-R (A-V) interval. Such a pacemaker, e.g. VDI or VDD, allows the atrium to control the heart's response rate, the ventricle being paced at the atrial rate up to a predetermined upper rate limit. Such synchronous pacers have incorporated means for dealing with high atrial rates, including "block" and "Wenckebach" techniques.

Another form of A-V or dual chamber pacer that has been utilized is the sequential pacemaker (DVI), which paces both the atrium and the ventricle with an appropriate A-V delay which is timed by the pacemaker. A number of commercial pacemakers have been introduced which are programmable to these and other known pacing modes. Each of the various operating modes is particularly adapted to certain circumstances that may arise in a given patient.

Since the dual sense-dual pace DDD pacemaker became commercially available, it has gained favor for the reason that it compensates for many of the disadvantages of other pacemaker modes. The classic DDD pacemaker is described in U.S. Pat. No. 4,920,965, Funke et al., in some detail. See also U.S. Pat. Nos. 4,539,991 and 4,554,921, incorporated herein by reference, which disclose other forms of DDD-type pacemakers.

More recently, the DDDR pacemaker has come to prominence. In this type of pacemaker, there is provided one or more sensors which enable the pacemaker to be rate responsive, such that the pacing interval, or escape interval, is varied as a function of one or more sensed rate-indicating parameters, rather than being fixed at a programmed value. In the DDDR pacemaker, both atrial and ventricular natural beats may occur so long as they occur prior to the respective rate responsive escape interval. See U.S. Pat. Nos. 4,467,807 and 4,951,667, which are illustrative of dual chamber rate responsive pacemakers.

There have also been disclosed multi-mode pacemaker designs having means for switching modes in response to changing patient conditions. Most dual chamber pacemakers are programmable to distinct modes, or switch automatically from one mode to another under certain prescribed conditions. See, for example, U.S. Pat. Nos. 4,527,568, and 4,920,965. However, there remains a substantial need in the pacing art for sensing the conditions under which a dual chamber pacemaker can or should be controlled to change mode, and for providing optimum flexibility for blending two or more modes of operation. Thus, instead of forcing the pacer to operate in a distinct mode until patient history enables switching to another distinct mode, the pacer would optimally be enabled to react on a cycle-to-cycle basis to sensed events. For example, while it is desirable to synchronize a delivered ventricular stimulus to a sensed atrial signal whenever possible, at the same time the pacemaker should be controlled to adopt another more optimum response whenever desired. Thus, if an atrial sensed beat occurs at too high a rate, or if retrograde conduction is determined, the pacemaker should have maximum flexibility for responding to this situation.

An area of dual chamber pacemakers that has received a great deal of attention in the prior art is that of placing a high (upper) limit on the atrial rate that will be tracked, i.e., the rate at which a ventricular stimulus will be delivered at a synchronized A-V interval following the sensed atrial beat. As discussed above, the Wenckebach-type response is incorporated into many commercial dual chamber pacemakers, which provides for lengthening the AV interval in response to atrial beats above the ventricular upper rate limit. This response provides a degree of synchronization, and maintains the ventricular stimulus rate within than the upper rate limit. As is known, this results in the occasional loss of a synchronized ventricular stimulus. See U.S. Pat. No. 4,554,921, for an example of a pacemaker comprising both Wenckebach and block modes of operation. Another means of genetrating synchronous ventricular pulses in response to high rate atrial signals, whether or not premature atrial contractions, is to extend the post-ventricular atrial refractory (PVARP). Likewise, the atrial refractory time can be extended past the time of anticipated retrograde P waves so as to avoid pacemaker mediated tachycardia. However, the extension of PVARP or the atrial refractory, lowers the upper rate limit for sensing atrial signals, and thus reduces the capability of the pacemaker to provide synchronous operation in response to atrial heartbeats which may be physiological. It is also known to vary PVARP, or the upper atrial limit, as a function of sensor data; See also Funke, U.S. Pat. No. 4,920,965, where the atrial pacing timeout and effective PVARP are varied as a function of the timing of certain sensed atrial signals.

In view of the prior art, there remains a great need for a pacing system which substantially continuously senses the atrial signal, i.e., minimizes PVARP, and maximizes synchronous tracking of physiological high rate atrial signals while limiting tracking of non-physiological high rate atrial signals. It is important that the pacemaker track only physiological atrial signals, and avoid tracking non-physiological atrial signals. Further, there is a need for a system which not only can automatically go into asynchronous operation when non-physiological atrial heartbeats are sensed, but can take active steps to re-synchronize the heart and return to synchronous operation as soon as possible.

BRIEF SUMMARY OF THE INVENTION

It is an object of this invention to provide a dual chamber pacing system which provides synchronous ventricular pacing in response to physiological atrial signals. The pacemaker continuously determines the rate of atrial signals and applies predetermined criteria to determine whether or not those atrial signals are physiological. Whenever a sensed atrial signal is determined to be physiological, the system then determines whether a ventricular stimulus, to be delivered at an AV interval following the atrial signal, would be at a ventricular rate which is also deemed physiological. Only if both the atrial rate and the determined ventricular rate are physiological is a tracked ventricular signal then delivered.

In accordance with the object of providing physiological synchronous tracking of the atrial signal, the system of this invention provides means for continuously determining a physiological rate as a function of atrial rate, whereby the physiological rate normally tracks sensed atrial signals. The system establishes dynamic decision rates which are coupled to the physiological rate, including a dynamic tracking limit and a dynamic pacing limit, which two limits define a physiological range. A dynamic Wenckebach range is also coupled to the physiological rate, whereby a Wenckebach response is provided for an atrial signal sensed in the Wenckebach range above the dynamic tracking limit. Means are further provided for delivering atrial pulses specifically timed to re-synchronize the heart in certain circumstances where the pacemaker has been operating in an asynchronous state.

It is another object of this invention to provide dual means for determining a patient's physiological rate. In accordance with this object, sensor rate information is used together with the atrial rate to determine the physiological rate, or sensor rate information is used to modify the atrial rate information. Alternately, the physiological rate can be determined as a function only of atrial rate, but the dynamic pacing limit can be overridden by sensor rate information.

It is another object of this invention to provide a dual chamber pacemaker having an improved Wenckebach response wherein most atrial signals having rates above the upper tracking limit are tracked by delivery of synchronous ventricular pulses at a rate corresponding to the upper tracking limit, while atrial signals that cannot be Wenckebach-synchronized are followed by asynchronous ventricular signals delivered at the normal pacing escape interval, whereby the average ventricular pacing rate is held below the upper tracking limit but no ventricular pace pulses are skipped.

It is another object of this invention to provide a pacemaker having means for carrying out a VA conduction test which is programmed to concurrently test for the conditions of retrograde conduction (RC) and far field R wave sensing (FFRS). The pacemaker automatically sets AV or VV interval to a different, predetermined interval for a number of consecutive cycles, and monitors the resulting VA interval. A measure of the resulting VA interval is determined and analyzed for VA equality, i.e., substantially equal VA intervals which indicate an RC or FFRS condition. When equality is determined, the pacemaker checks the measure of VA interval with stored RC and FFRS criteria, to determine whether one of them is verified. Respective corrective steps are taken when either condition is verified.

BRIEF DESCRIPTION OF THE DRAWINGS

FIGS. 5a, 5b and 5c are curves illustrating the dynamic pacing limit (DPL) as a function of physiological rate.

DESCRIPTION OF THE PREFERRED EMBODIMENTS

Figure 1:
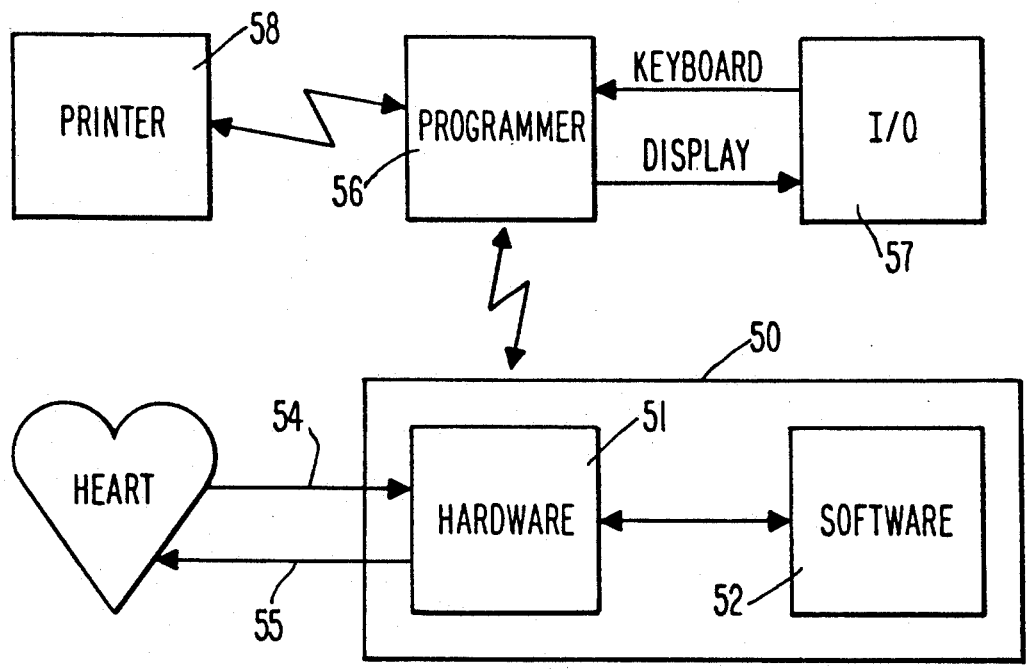
FIG. 1 is a block diagram of the overall system of the invention, showing the environment in which the pacemaker software operates.

In the detailed description of the pacing system of this invention, as well as the illustrative figures, the following acronyms, abbreviations and symbols are utilized;

| Events | |
|---|---|
| V-event | VS or VP |
| VS | any Ventricular Sense |
| NVS | Normal Ventricular Sense (physiologic) |
| TVS | Tachy Ventricular Sense |
| VES | Ventricular Extra Systole |
| NVES | Normal Ventricular Extra Systole |
| TVES | Tachy Ventricular Extra Systole |
| VP | Ventricular Pace |
| A-event | AS or AP |
| AS | any Atrial Sense |
| NAS | Normal Atrial Sense (physiologic and synchronous) |
| NAB | Normal Atrial Blocked sense (physiologic and asynchronous |
| TAS | Tachy Atrial Sense |
| BAS | Brady Atrial Sense |
| UAS | Unidentified Atrial Sense |
| PAC | Premature Atrial Contraction (first TAS) |
| NOA | No Atrial event |
| AP | Atrial Pace |
| ASP | Atrial Sync Pace |
| WBS | Wenckebach Sense (WB range and synchronous) |
| WBB | Wenckebach Block sense (WB range and asynchronous |
| TS | T-wave Sense |
| APL | Atrial Pace Limit |
| Rates and Intervals: | |
| WBd | Wenckebach distance |
| TRd | Tracking distance |
| FWd | Flywheel distance |
| ESC_ rate | Escape rate |
| Phys_ rate | Physiological rate |
| Phys_ range | Range of Physiological Rates |
| LPL | Lower Pacing Limit |
| DPL | Dynamic Pacing Limit |
| UPL | Upper Pacing Limit |
| LTL | Lower Tracking Limit |
| DTL | Dynamic Tracking Limit |
| UTL | Upper Tracking Limit |
| DWL | Dynamic Wenckebach Limit |
| ANSP | Atrial Non Sensing Period |
| VNSP | Ventricular Non Sensing Period |
| PVARP | Post Ventricular Atrial Refractory Period |
| PVAB | Post Ventricular Atrial Blank |
| AA, AA_Int | interval between two consecutive atrial events |
| APL_int | minimum interval between an AS and an ASP |
| VA, VA_int | interval between consecutive ventricular- and atrial events |
| VV, VV_int | interval between two consecutive ventricular events (also referred to as V-V) |
| AV, AV_int | interval between consecutive atrial- and ventricular events (also referred to as AV delay |
| Rate Responsive Items: | |
| RR | Rate Responsive |
| RR_sensor | Rate, e.g., QT or Activity |
| QT | QT_interval |
| ACT | Activity level in the time-domain |
| Other: | |
| PMT | Pacemaker Mediated Tachycardia |
| RDAN | Rate Drop At Night |
| RC | Retrograde Conduction |
| RCD | Retrograde Conduction Detection |
| FFRS | Far Field R-wave Sense |
| WB | Wenckebach |
| int | interval |

| | -continued |
|---|---|
| cycle | period between two successive atrial events (for atrial modes), or two successive ventricular events (for all other modes) |
| AV-sequence | AS, AP or ASP followed by VS, or NAS, AP or ASP followed by VP |
| WB-sequence | WBS followed by VS or VP |
| AV(AA) | AV-delay as a function of A-A interval |
| AV_ext | AV extension |
| synchronous | state in which every A-event is followed by a V-event |
| asynchronous | A-event and V-event are not related |
| programmable | the value can be programmed by telemetry |
| Used Symbols: | |
| ∩ | AS |
| ∧ | NAS |
| ▲ | PAC, TAS, BAS, UAS, NAB |
| △ | WBS |
| ⚠ | WBB |
| ∪ | VS |
| V | NVS, TVS |
| ▼ | VES, TVES |
| — | refractory period, blanking period |
| ⌊ | AP and refractory period |
| ⌐ | VP and refractory period |
| ▒ | physiologic area |
| ↻ | restart of a cycle |

The subject invention is illustrated using ventricular-based timing, but it is to be understood that a dual chamber pacemaker using atrial-based timing likewise falls within the scope of this invention. For example, the generation of a ventricular escape interval may be done by timing an interval from a last ventricular event to a scheduled ventricular pulse; or it may be timed as an A-A interval less AV delay. Likewise, the VV interval can be determined by timing a VA interval plus AV interval. Thus, although the invention is illustrated in terms of a ventricular-based pacemaker, it is equally applicable to an atrial-based timing arrangement. See also the discussion below in connection with FIGS. 12a-d.

The pacing system of this invention is software-based, i.e., the software controls all functions through the hardware, as illustrated in FIG. 1. The timing diagrams which are used to illustrate functions, and which incorporate symbols as set forth above, are the equivalent of flow charts in showing the logical steps carried out by the software in response to parameters that control the pacing behavior. These timing diagrams correspond to the IEEE 830-1984 standard for software requirement specifications. Referring specifically to FIG. 1, the pacemaker 50 is shown as having a component hardware portion 51 and a software portion 52, the two portions being interconnected. The software is parameter-driven, i.e., there are numerous parameters that control the pacing behavior, diagnostic functions, etc. The hardware is interconnected with the patient's heart by one or more electrodes 55, and one or more sensor connections 54. As is well understood in the art, for a dual chamber pacemaker, there are generally two leads, an atrial lead and a ventricular lead, each lead having at least one electrode unipole or bipole positioned in the heart. The line 54 is illustrated as leading to the heart, as in a QTtype sensor arrangement, but may be attached to the outside case of the pacemaker or may couple to any other available sensor for sensing body parameter information used in rate responsive pacing systems. Further, in the preferred embodiment of the pacing system of this invention, sensor link 54 may comprise a pair of sensors, e.g., QT plus activity, as set forth in U.S. Pat. No. 5,065,759.

As further illustrated in FIG. 1, the pacer 50 is in telemetric communication with a programmer 56. The user can select parameters and program them through programmer 56, and can also interrogate parameter and diagnostic data from the implanted pacemaker. Interrogated information from the pacer can be coupled by telemetry directly to a printer 58. Input/output devices 57 are used to input information by the user to the programmer, or to display information received by the programmer from the pacemaker.

Figure 2:
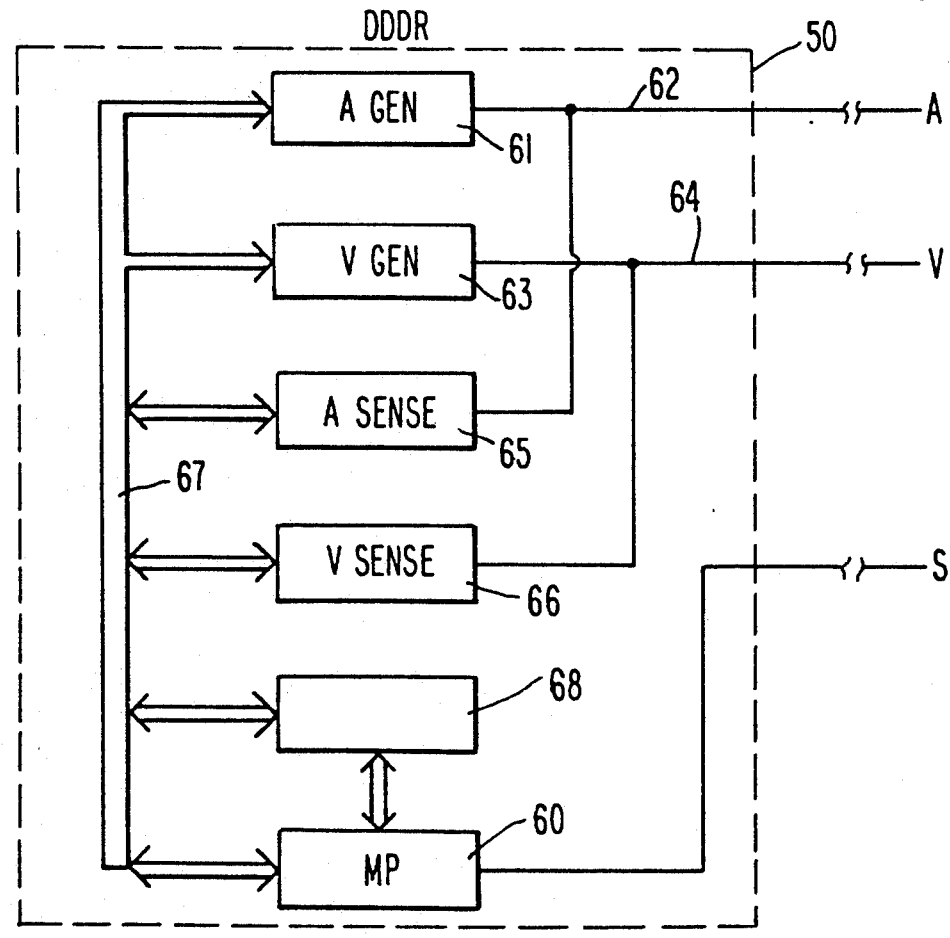
FIG. 2 is a block diagram which illustrates basic components of the pacemaker of this invention, together with leads and a sensor for delivering signals to and/or receiving signals from the patient.

Referring to FIG. 2, there is shown a basic block diagram of primary hardware components of a DDDR pacer 50. An atrial generator 61 is shown, having an output connected to lead 62 which communicates with the patient's atrium. An A sense amplifier 65 is illustrated also connected to atrial lead 62. A ventricular generator is illustrated which is connected to the patient's ventricle through lead 64. V sense amplifier 66 is also connected to lead 64, to receive and sense signals from the patient's ventricle. In one embodiment of this invention which preferably incorporates QT rate control, V sense block 66 also includes means for picking out and determining the timing of the evoked T wave. Generators 61 and 63 and sense blocks 65 and 66 are interconnected with microprocessor system 60, which microprocessor has software which is parameter-driven to control the operation of the hardware units. Microprocessor system 60 may be interconnected with hardware logic and/or timing circuits 68. The microprocessor system suitably consists of a D43 microprocessor with 4k byte ROM and 624 bytes RAM (MC146805E2 compatible); and an M05 memory chip with 4k byte ROM and 256 bytes RAM. It is preferred that the operating software fit in 8k byte ROM, and have available for use 624 bytes of RAM; 256 bytes of RAM are held unused to enable future RAM routines (executable code located in RAM). In a manner well known in the art, the software contains a number of strategic places where escape points to a RAM routine are available. As affects the scope of this invention, the degree to which software supplants hardware, or vice versa, is a matter of design choice. Thus, for the many timing functions that are carried out in the pacing system of this invention, it is to be understood that the microprocessor may have built in timing circuits, or suitably may control external hardware timer circuits. Software control of pacing function is well known in the art, such that the following detailed discussions of the software specifications enable one of ordinary skill in this art area to design a system for carrying out the functions within the scope of the invention. Data inputted from programmer 56 is stored in memory associated with microprocessor.

Still referring to FIG. 2, there is shown a sensor S, indicated as providing an input to microprocessor system 60. Sensor S represents one or more sensors for monitoring one or more body parameters known to be indicative of desired pacing rate. Sensor S is illustrated as being outside the pacemaker, but may be physically located inside the pacemaker casing, as with certain activity sensors. Alternately, as is the case with the Q-T-type rate responsive pacemaker, the "sensor" information is actually obtained from the ventricular lead, by extracting timing information relating to the Q-T interval. As used in the practice of this invention, the term sensor or sensor signal may refer to information obtained from any available rate responsive sensor-type source. Also, as used in the claims hereto, the term "rate signal" may refer to a signal deriving its information from either or both a sensor source and the sensed atrial rate.

In general, the pacing system of this invention can be programmed to operate in any one of the following pacing modes: OOO, AOO, AAI, AAT, VOO, VVI, VVT, DOO, DDI, DVI, VDD, DDD. OOO is a passive mode; AOO, AAI and AAT are atrial modes; VOO, VVI and VVT are ventricular modes; DOO, DDI and DVI are non-tracking dual chamber modes; and VDD and DDD are tracking dual chamber modes. The preferred embodiments of this invention are illustrated primarily in connection with the tracking dual chamber modes, VDD and DDD. For these modes, the cycle is ventricular-based, i.e., starts at VS and VP; an AS inhibits the atrial pace; a VS inhibits the ventricular pace; and an ANSP starts at NAS, WBS, AP, ASP, VS, or VP, and ends at the end of PVARP.

Figure 3:
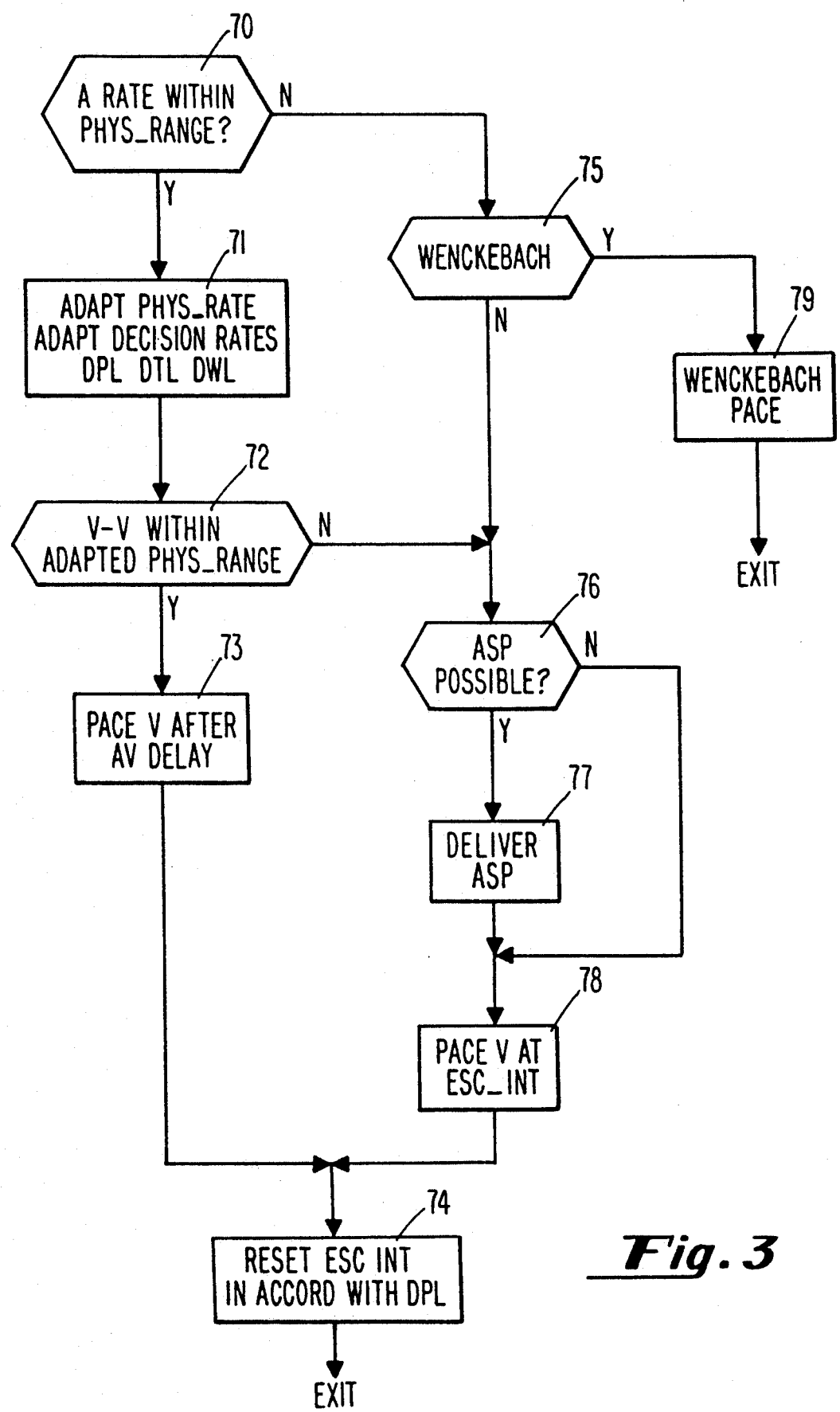
FIG. 3 is a simplified flow diagram illustrating dynamic AV tracking in DDD or VDD modes of the pacing system of this invention.

Referring now to FIG. 3, there is shown a flow diagram illustrating the procedure following an atrial event, and in particular illustrating tracking when an atrial event is determined to be physiological. At block 70, the software first determines whether an atrial rate is within the phys_range limits. By atrial rate, reference is made to the rate corresponding to the interval from a prior atrial event to the atrial event under examination. The premise at this point is that any atrial event that has occurred has been recognized by the pacemaker, i.e., no atrial event has been blocked out such that it is not recognized. In order to achieve this, the blanking of the atrial channel, such as by a PVARP, must be very small, such that there is substantially continuous sensing of the atrial channel. While in practice some PVARP is maintained, in the preferred embodiment of this invention, PVARP is limited to a very short blanking duration following a ventricular event (2-10 ms). Thus, at block 70, the time interval from the prior atrial event to the current atrial event is determined, and compared to a predetermined phys_range, which range can be expressed either in terms of rate values or corresponding time intervals. As discussed above, and as amplified in much greater detail below, the phys_range limits comprise a lower limit referred to as dynamic pacing limit (DPL) and an upper range limit referred to as dynamic tracking limit (DTL). The DTL determines how high an atrial rate can be tracked, while DPL sets the pacing interval. Also, the change of A rate is checked to see whether the change is physiologic.

If the A rate is within the phys_range and change limits, the software branches to block 71, where the phys_rate is adapted as a function of the just determined atrial rate; also the decision rates which are coupled to the phys_rate are adapted, i.e., DPL, DTL and DWL are adapted. The criteria for adapting the phys_rate are set forth in connection with the discussion below of FIG. 4; the coupling of the decision rates to the phys_rate is discussed in relation to FIGS. 5a through 9. After adapting the phys_$_{rate\ and\ the\ decision}$ rates, at 72, it is determined whether the synchronized ventricular pulse would have a rate within the adapted phys—range. Thus, the AV interval is added to the time of the atrial event, and the projected synchronous V stimulus time is compared with the prior V event to determine the V-V interval, and thus the V rate. Only if the determined V rate is within the adapted physiological range (DPL to DTL) does the software branch to block 73, to control the delivery of a ventricular pace after timeout of an AV-delay. If V-V is not within the phys—range, the program branches to block 76.

Figure 7A:
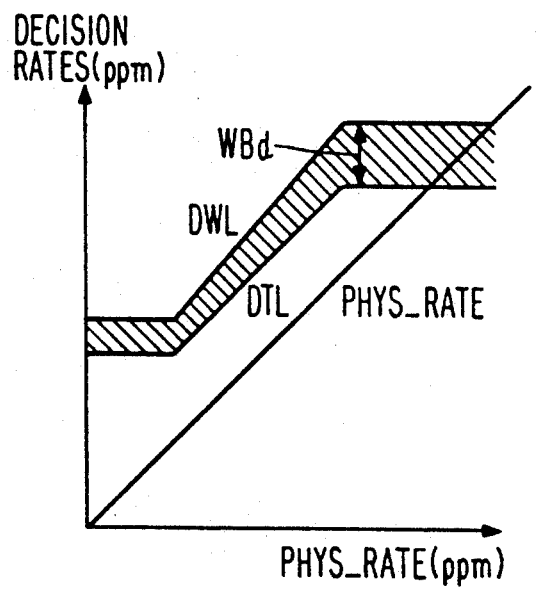
FIGS. 7a and 7b are graphs illustrating the Wenckebach range of spontaneous rates which result in Wenckebach behavior for VDD and DDD modes of the pacing system of this invention.
Figure 7B:
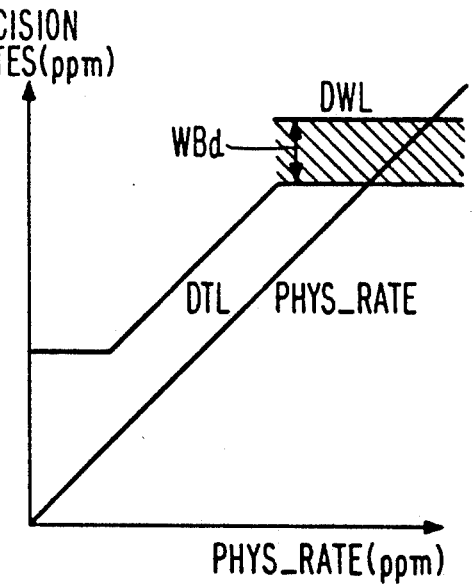

Coming back to block 70, if the A rate is not within the phys—range and rate change limits, the software branches to block 75, where it is determined whether the atrial event has fallen within the Wenckebach range, WBd (See FIGS. 7a, 7b). If yes, a Wenckebach pace is delivered as indicated at block 79, in accordance with the Wenckebach criteria discussed in more detail hereinbelow. If no, the program proceeds to block 76, where it is determined whether an Atrial Sync Pulse (ASP) can be delivered. The criteria for delivery of an ASP are set forth hereinbelow. If these criteria are met, an ASP is delivered, as indicated at block 77. If ASP is not possible, the program branches to block 78, where the ventricle is paced at the escape—interval, which interval is normally set by the dynamic pacing limit. Following this, the escape interval is reset in accordance with DPL, as indicated at block 74.

Figure 4A:
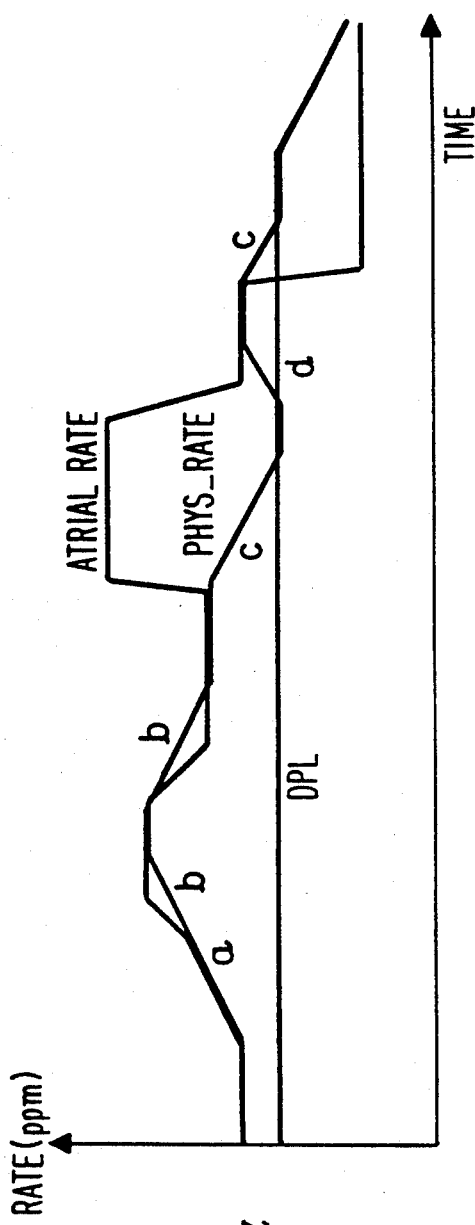
FIGS. 4a and 4b are curves illustrating how the physiological rate tracks atrial rate in DDD mode operation of the pacing system of this invention.
Figure 4B:
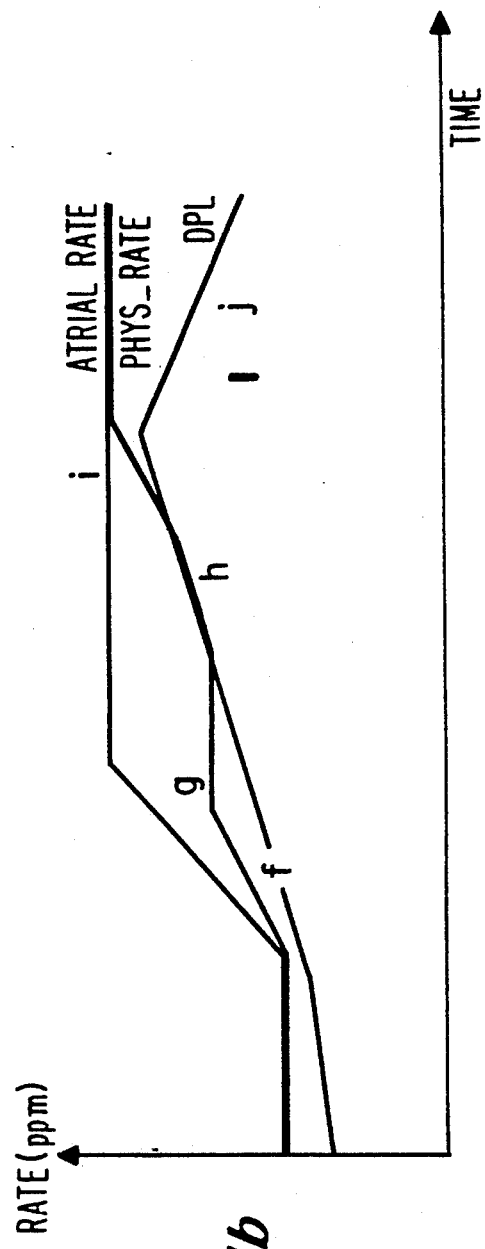

Referring now to FIGS. 4a and 4b, there are illustrated the criteria for determining whether the A rate is physiological, and for adapting the phys—rate in response to physiological atrial rates. The curves of FIGS. 4a and 4b present examples of how phys—rate behaves in the DDD mode; for purposes of illustration, flywheel is off, i.e., DPL does not depend on phys—rate, but is only controlled by the RR algorithm. Note that for non-tracking atrial modes, phys—rate preferably simply follows the atrial rate; for non-tracking ventricular modes, as well as for non-tracking dual chamber modes, the phys—rate follows the ventricular rate. In a first embodiment of this invention, as illustrated here, for tracking dual chamber modes, in the sync state, the phys—rate follows the atrial rate, while in the async state the phys—rate follows the ventricular rate. Phys—rate may generally be a function of atrial rate, as illustrated, but it is within the scope of the invention that it may follow the ventricular rate during sync mode operation, since physiological atrial senses are conducted to produce ventricular pulses. Thus, as used in the claims appended hereto, when it is said that the phys—rate is a function of atrial rate, this also embraces any system which determines a phys—rate based on synchronized V events. Other criteria for determining phys—rate in the preferred embodiment are as follows:

(a) If there is a pathologic spontaneous rate, phys—rate follows DPL, except after a PAC (the first TAS) phys-rate shall be frozen for one cycle; and after a VES phys—rate shall be frozen for one cycle.

(b) In the tracking modes of VDD and DDD, if there is a spontaneous rate in the WB—range, meaning that the system is in a WB state, then the phys—rate shall be frozen (maintained constant), except that if there is a spontaneous rate in the WB range and the RR algorithm forces DPL to exceed phys—rate, then phys—rate shall follow DPL.

(c) If there is a physiological spontaneous rate, phys—rate follows that rate.

(d) If there is a paced rate, phys—rate follows DPL (the actual pacing rate).

(e) When phys—rate changes, it increases or decreases incrementally subject to a maximum phys—rate change, e.g., ±2 ppm per cycle. Since the phys—rate follows physiological spontaneous rates with a limited speed, it represents average physiological rate.

Referring again to FIGS. 4a and 4b, at portion (a), the rate is physiologic, so it is followed by phys—rate. As thus shown, the physiological rate is increasing linearly with the spontaneous atrial rate. At portion (b), the rate remains physiologic, but it changes faster than the phys—rate can change. Under these conditions, phys—rate is changing at its maximum rate (±2 ppm/cycle), as are the decision rates that are coupled to it. At the portion of the curves indicated at (c), the atrial rate becomes pathologic, such that the phys—rate ramps down incrementally to DPL. At (d), where the atrial rate again becomes physiologic, phys—rate increments back up to and follows the phys—rate. At (e), the spontaneous rate drops below DPL, such that pacing pulses are delivered at the DPL rate, and phys—rate now follows DPL. Note that for an abrupt drop in atrial rate below DPL, phys—rate decrements down to DPL.

Figure 9:
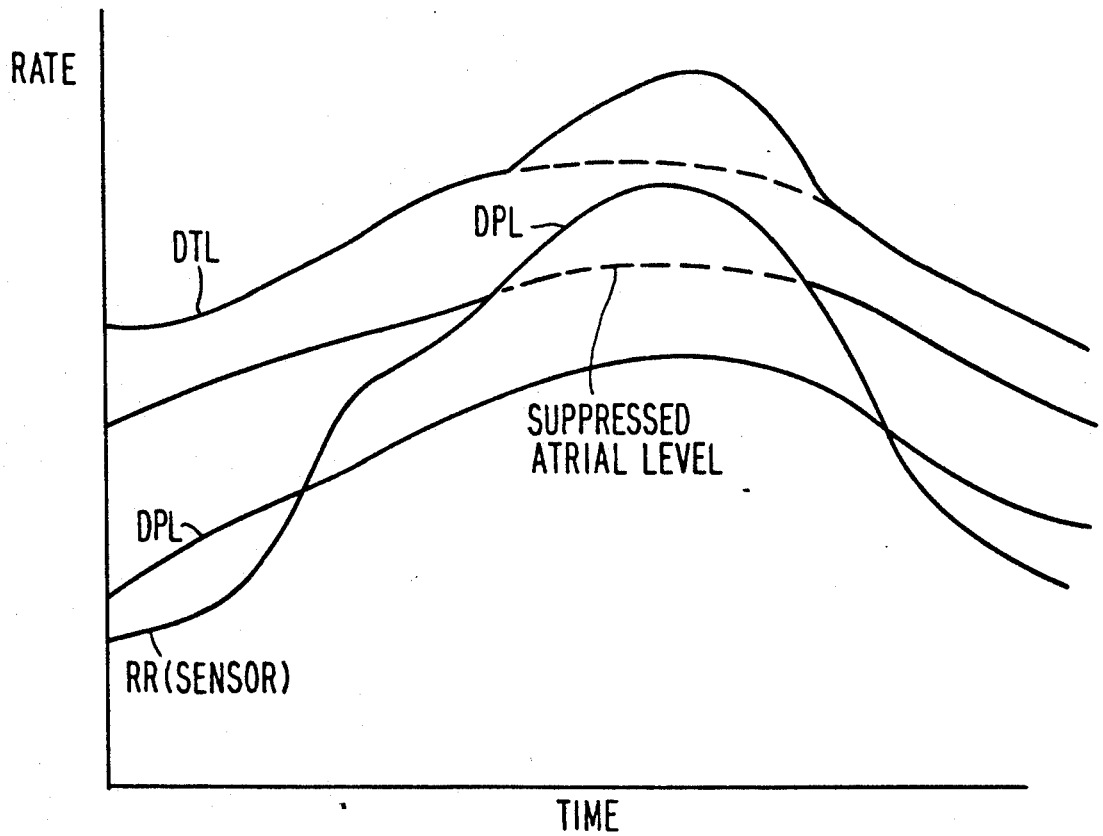
FIG. 9 is a graph illustrating an embodiment wherein physiological rate is normally determined as a function only of atrial activity, subject to sensor information modifying the physiological rate and the determination of decision rates.

Referring to FIG. 4b, at portion (f) the atrial rate is physiologic, but is changing faster than the phys—rate can change. Note also that DPL is ramping up at this point, due to the RR (sensor) input. At portion (g), the atrial rate has risen into the WB area, so phys—rate is frozen at the last value before entry into the WB range. At (h), the prior frozen phys—rate is exceeded by the DPL which is being pushed up by RR, such that phys—rate now follows DPL. This leads to interval (i), where the increased DPL elevates the Wenckebach range such that the spontaneous atrial rate no longer falls in the WB area, but becomes physiologic again. At this point, the phys—rate increments up to and then follows the spontaneous rate which is now considered physiological. This behavior continues, even into the time period marked (j), where DPL decreases because RR calls for a decreasing pacing rate. Reference is also made to FIG. 9, which illustrates the embodiment where phys—rate follows atrial rate, but the sensor information can override the influence of the atrial rate in setting DPL, or indeed phys—rate and DTL also.

Referring back to block 70 of FIG. 3, A rate is considered to be physiologic if it is between the maximum and minimum (DPL) value set during the last cycle; the average rate-change does not exceed a predetermined maximum; and the beat-to-beat rate-change does not exceed a predetermined maximum. These criteria, plus the criteria of adjusting the phys—rate by a limited amount each cycle, results in a generation of a phys—rate which substantially continuously represents the average rate of atrial events which are non-pathological. It is to be noted that other criteria can, of course, be adopted for generating the equivalent of this phys—rate for tracking purposes. Thus, the rate parameter can be collected over a period of n cycles, the average taken, and the phys—rate adjusted only after every nth cycle. Further, the acceptable limits on rate-change, and the limits on incremental phys—rate change, can be made a function of atrial rate itself, e.g. at higher atrial rates greater limits are permitted. Alternately, the phys—rate can be set in terms of atrial rate and sensor rate (RR), in which case it is still a function of atrial rate. An important feature is that data be stored and substantially continuously updated by the microprocessor 60, so as to accurately maintain a true indicator of the patient's physiological rate. As stated above, this physiological rate may be in fact derived by determination of V-V interval when in a sync mode (VDD or DDD), but still is a function of atrial rate. While in the preferred embodiment, phys_rate is updated every cycle, the term "function of atrial rate" is not so limited.

The pacing system of this invention comprises means to decide whether atrial or ventricular sensed events are in the defined physiologic, pathologic or Wenckebach range. The response of a pacemaker varies depending upon this determination, in a manner set forth below. In single chamber modes, the decision of where the atrial or ventricular sense falls does not influence pacing behavior, i.e., any sense inhibits the channel where it is sensed. However, in the dual chamber tracking modes, physiologic A senses are conducted to the ventricle, while pathologic A senses are not. In the preferred embodiment, the actual atrial rate is compared to the three decision rates:

dynamic pacing limit (DPL)
dynamic tracking limit (DTL)
dynamic Wenckebach limit (DWL).

In practice, these three decision rates are coupled to the phys_rate, and allow discrimination of the following four rate ranges:

(a) pathologic low rate range for rates below DPL (including hysteresis, when applicable). In the VDD and DDD modes, such pathologic low rate A senses are not conducted to the ventricle.

(b) physiologic range for rates between DPL (including hysteresis, when applicable) and DTL. In the VDD and DDD modes, atrial rates in this range can be conducted to the ventricle, and are so conducted when possible (when the resulting V rate is within the physiologic range).

(c) the Wenckebach range for rates between DTL and DWL. In VDD and DDD modes, rates in this range result in Wenckebach behavior.

(d) pathologic high rate range for rates exceeding DWL, when Wenckebach is programmed active, or DTL when Wenckebach is not active. In the VDD and DDD modes, such pathologic high rates are not conducted to the ventricle. The following FIGS. 5a, 5b and 5c; 6; 7a and 7b; 8 and 9 illustrate the operation of these decision rates.

Referring first to FIGS. 5a, 5b and 5c, the dynamic pacing limit is illustrated for the circumstances where it is RR controlled (FIG. 5a); "flywheel" controlled (FIG. 5b); and controlled by both RR and flywheel (FIG. 5c). In FIG. 5a, the dynamic pacing limit is shown as only RR controlled. As represented here, it is not a function of phys_rate, but for any given phys_rate may vary between programmable values of LPL and UPL as a function of the sensed parameter or parameters. In the FW controlled mode of FIG. 5b, DPL tracks the phys_rate, and thus the atrial rate, maintaining a distance FWd below the phys_rate as per conventional flywheel tracking arrangements. FWd is a programmable distance. Note that DPL stays constant at LPL for all rates up to a rate corresponding to the lowest phys_rate where a flywheel window of FWd is established. In the situation where DPL is both RR and FW controlled, as illustrated in FIG. 5c, the dynamic DPL can also be shifted up and down as a function of the sensor information, between the LPL and UPL limits. Indeed, the RR control can override a phys_rate which reflects only A rate, for most of the range up to UPL.

The dynamic pacing limit is generally used to establish escape rate, for both atrial and ventricular pacing. However, the escape rate can be modulated under certain circumstances, e.g. the VA conduction test; hysteresis; and QT evoking. The following rules apply to DPL:

(1) If both flywheel and rate response are off, DPL is incremented downward to become equal to LPL.

(2) If only flywheel is on, (a) when there is no physiologic spontaneous rate, DPL steps downward toward LPL; (b) when there is a physiologic spontaneous rate, DPL follows phys_rate at the coupled flywheel distance (FWd).

(3) If only rate response is on, DPL is controlled solely by the RR algorithm.

(4) If flywheel and rate response are on, (a) if there is no physiologic spontaneous rate, DPL is controlled by the RR algorithm; and (b) if there is a physiologic spontaneous rate, DPL follows phys_rate at the flywheel distance, unless the RR algorithm indicates a higher rate.

(5) DPL rate increase shall not exceed (a) phys_rate change when a rate increase is caused by flywheel, or (b) pacing acceleration when rate increase is caused by rate response.

(6) DPL rate decrease shall not exceed pacing deceleration.

(7) DPL is limited at UPL.

(8) Since LPL can be changed due to a tachycardia response or rate drop at night, DPL can be stepped up or down relative to LPL.

Figure 6:
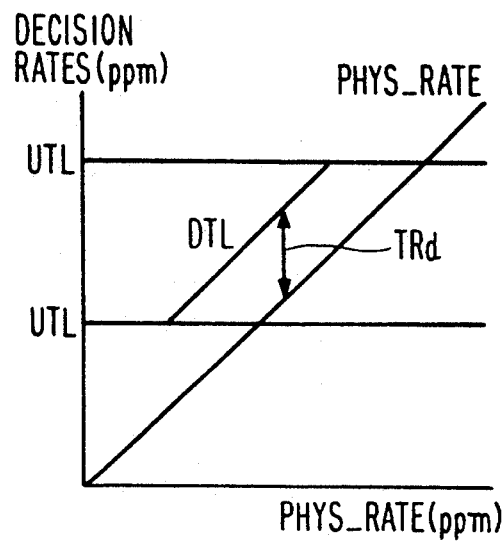
FIG. 6 is a curve illustrating the variation of dynamic tracking limit (DTL) as a function of physiological rate.

Referring now to FIG. 6 there is shown a curve showing the dynamic tracking limit (DTL) as a function of phys_rate. DTL is the rate which defines the upper limit of the physiologic range, such that atrial sensed events having rates below DTL can be candidates for tracking to the ventricle. Subject to the LTL and UTL tracking limits, DTL preferably varies linearly with phys_rate, and is equal to phys_rate plus the tracking distance TRd (programmable). It is to be noted that in the pacemaker of this invention, DTL can be made fixed by programming UTL and LTL to equal values.

Referring to FIGS. 7a and 7b, there is illustrated the dynamic Wenckebach limit for both the dynamic case and the fixed case. Spontaneous rates between the DTL and DWL are interpreted to control Wenckebach behavior for the VDD and DDD modes. In both the dynamic and the fixed cases, the Wenckebach distance (WBd) is programmed as a constant number of ms, such that DWL_int shall be equal to DTL_int minus WBd. As seen in FIG. 7a, where the WB mode is dynamic, DWL is above DTL over the entire phys_rate range, the rate range increasing with increasing rate because the interval corresponding to WBd remains fixed. In the WB fixed mode, DWL is placed above DTL, but WB is only active in the case where DTL has become equal to UTL, i.e., a physiologic rate has driven DTL up to the UTL. Note that since phys_rate change is limited (e.g., 2 ppm/cycle), Wenckebach mode operation cannot be reached unless the atrial rate stays physiological and moves up the DTL range toward UTL. The improved Wenckebach mode as provided by this invention is discussed in further detail in connection with FIGS. 16a and 16b.

Figure 8:
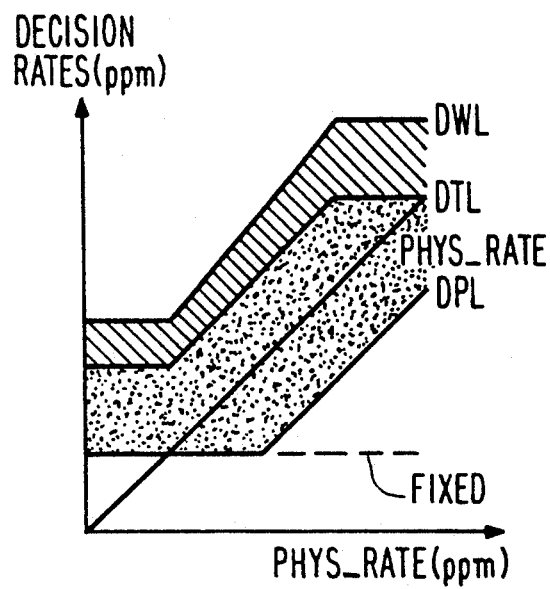
FIG. 8 is a graph illustrating the variation of decision rates (DPL, DTL and DWL) with physiological rate in the pacing system of this invention.

Referring now to FIGS. 8 and 9, there is shown an overview of the decision rates, and how they track phys—rate. FIG. 8 illustrates the variation of the three decision rates as a function of phys—rate, in tracking situations, with flywheel on. The range of rates below DPL is the pathologic low rate range. Note that if flywheel is off, then DPL is fixed at a constant lower rate, as indicated by the dashed line. The dynamic range between DPL and DTL is the physiologic range, for which sensed atrial events are tracked; it is programmed not to exceed a predetermined limit (e.g., 30 bpm), so as to limit the variation in ventricular pacing rate when there is a change from async to sync operation. The dynamic range between DTL and DWL is the Wenckebach range. It is to be noted that the RR algorithm can increase DPL, and thereby decrease the flywheel distance, as illustrated in FIG. 9. Indeed, the RR algorithm can override phys—rate as well as DPL, and cause a corresponding increase DTL up to the programmed UTL value. Although not shown in these figures, it is to be noted that in a stable pacing situation, when RR is off, DPL steps toward LPL; also, phys—rate follows DPL, so the system becomes stable when both DPL and phys—rate have reached LPL. In the preferred embodiment, the dynamic rates change linearly with physiological rate, but may also vary non-linearly within the scope of the invention.

Figure 10A:
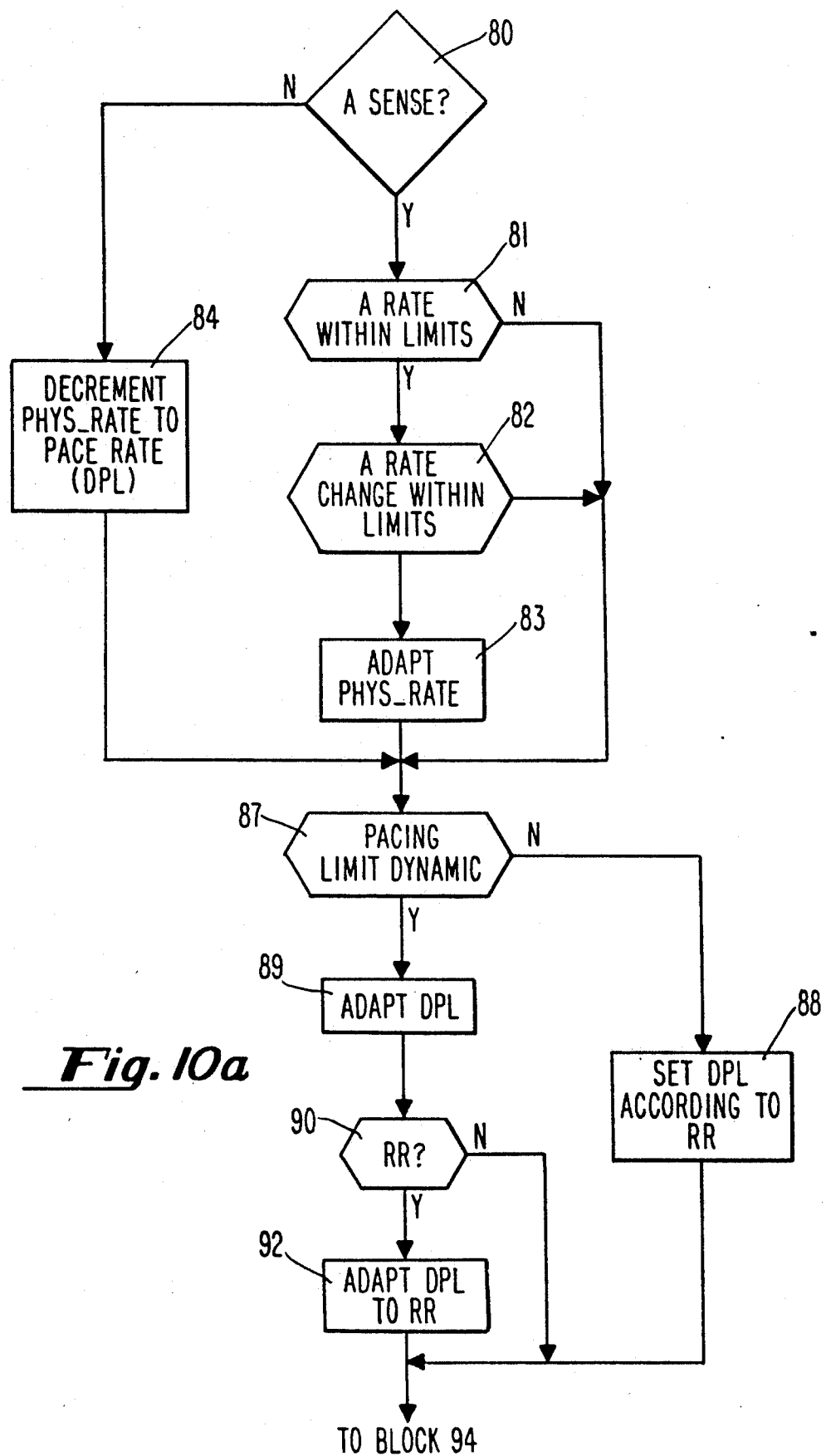
FIGS. 10a and 10b constitute flow diagrams illustrating software steps in setting decision rates in accordance with the pacing system of this invention.
Figure 10B:
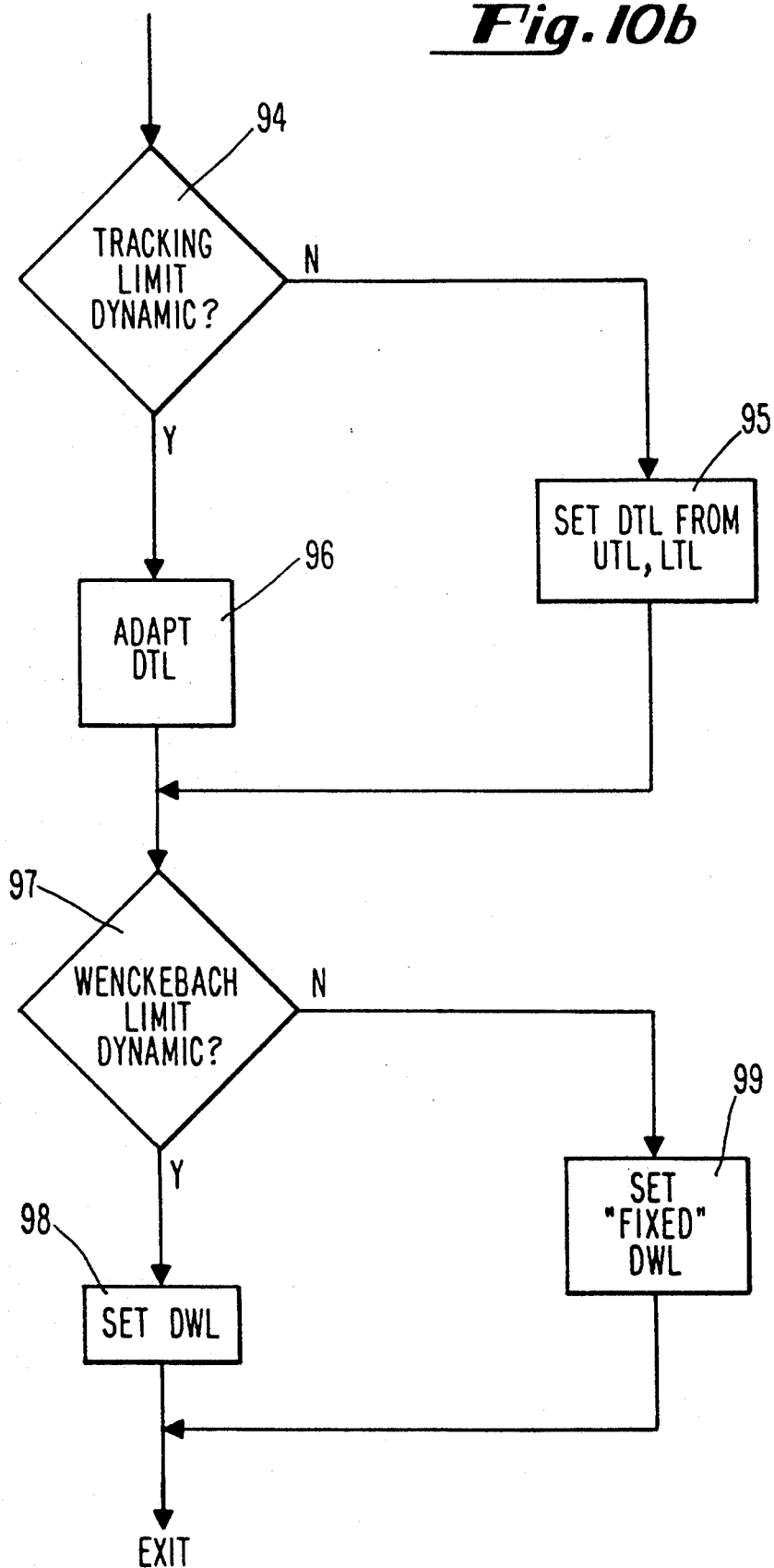

Referring now to FIGS. 10a and 10b, there is shown a flow diagram that illustrates adaptation of phys—rate and coupling of the decision rates to phys—rate. At block 80, it is determined whether the A-event has been an A sense. If no, meaning that the atrial escape interval timed out and an atrial stimulus was delivered, the software branches to 84 and decrements the phys—rate to the pace rate (DPL). Thus, as said above, in a stable pacing situation, the phys—rate becomes DPL.

Returning to block 80, if there has been an A sense, the program goes to 81, where it is determined whether the atrial rate is within the range limits, i.e., within the physiological range as adjusted during the last pacing cycle. If no, the program skips to 87; if yes, the program goes to 82 and determines whether the atrial rate change is within predetermined physiologic limits. As discussed above, an atrial event is not considered physiological even if within the range, if the jump in rate exceeds a predetermined (programmable) limit, up or down. If the atrial rate is not within the limits, the program branches to block 87; if it is within limits, establishing it as physiological, the program goes to block 83 where the phys—rate is adapted, as per the above criteria. At block 87, it is determined whether the pacing limit is programmed dynamic. If no, at 88 the DPL is set according to the RR data. In an alternate embodiment, DTL can be concurrently adjusted as a function of the RR data. If the pacing limit is dynamic, meaning that it is coupled to the phys—rate, the program goes to block 89, where DPL is adapted, e.g., it is moved linearly with phys—rate. Note that if the atrial sense for the current cycle is not physiological, then phys—rate has not been adapted, and DPL is not adapted at 89. The pacing deceleration and acceleration is limited in the same way as phys—rate change when in flywheel.

At block 90, it is determined whether rate response (RR) is active (in the manner shown in FIG. 9). If yes, DPL is adapted to RR as indicated at 92. Here, pacing rate changes are limited by the RR algorithm.

The program proceeds to 94, where it is determined whether the tracking limit is dynamic. If no, meaning that DTL is fixed, then DTL is set equal to the programmed value of UTL and LTL, at block 95. If tracking limit is dynamic, DTL is adapted at 96, i.e. DTL is set equal to phys—rate plus the tracking distance, subject to limitations of LTL and UTL.

The program proceeds to block 97, where it is determined whether the Wenckebach limit is dynamic. If yes, DWL is set at 98, i.e., DWL—int is equal to DTL—int minus the Wenckebach distance (remembering that Wenckebach range is set in constant ms). If, at 97, it is determined that Wenckebach limit is fixed, the program branches to 99, where the fixed DWL is set at a rate above DTL corresponding to WBd. As stated above, in this situation, WB is only active in the case that physiologic rate has driven DTL up to UTL.

From the above, it is seen that the decision of whether or not to track a sensed atrial signal and deliver a synchronous ventricular pace pulse is preferably based on determined atrial rate. By contrast, in a strictly timing-based pacer, an atrial sense may occur at a time relative to the last sensed atrial event so as to appear to be physiological, but yet be preceded by an earlier atrial event that occurred during PVARP, but was not accounted for. The pacer of this invention minimizes PVARP to PVAB (post-ventricular atrial blanking) of, e.g., preferably 6 ms, and no more than 10 ms, so that substantially all spontaneous atrial events are sensed. PVAB is set as small as possible, consistent with avoidance as far field R waves. As a result, atrial rate can be determined substantially continuously, and an AS which has occurs safely after the last tracked AS may still be rejected as non-physiological if there is an intervening AS. The combination of tracking as a function of rate (i.e., decision rates are a function of atrial rate, not atrial timing) and substantially continuous sensing provides an optimized control for selecting which atrial senses are tracked.

Figure 11A:
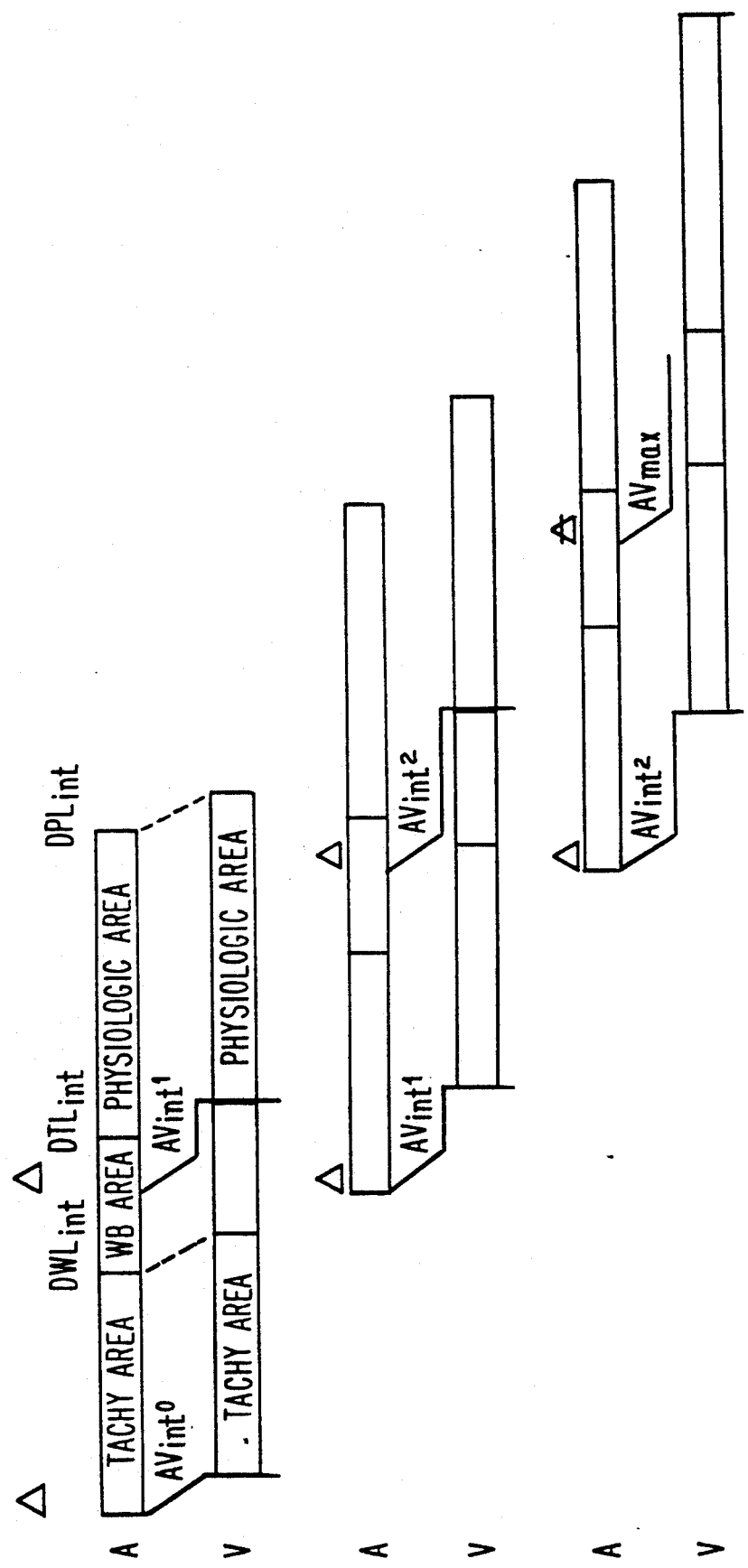
FIGS. 11a and 11b are timing diagrams which illustrate the pacemaker logic in responding to different atrial and ventricular events.
Figure 11B:
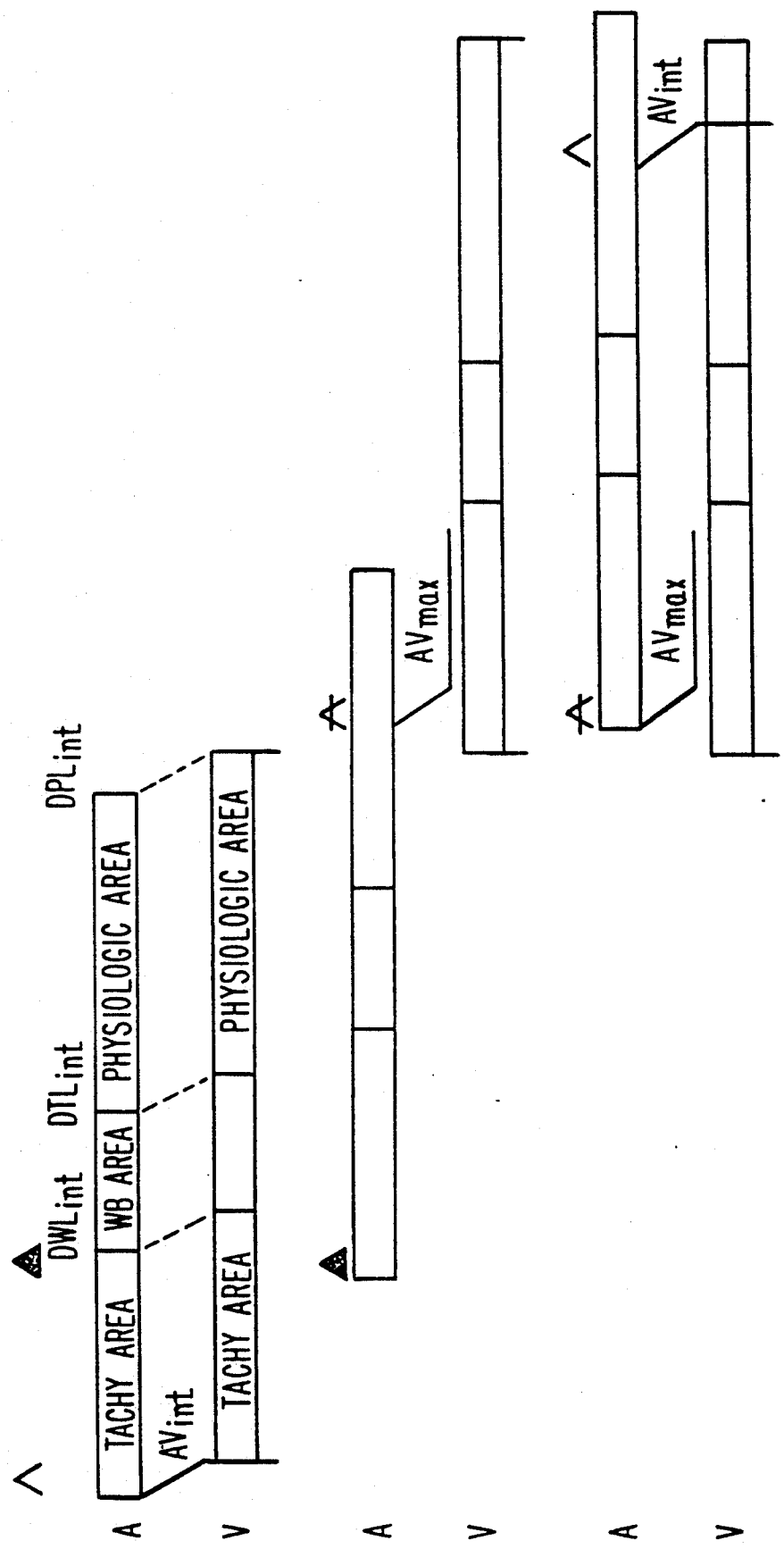

FIGS. 11a-b and 12a-d present timing diagrams which illustrate the operation of the pacemaker in the time domain. Referring now to FIGS. 11a and 11b, there are shown sets of timing diagrams which illustrate how the pacemaker of this invention carries out timing for the atrial and ventricular channels, and how the rate ranges discussed above correlate to time intervals. Each of these figures illustrates three consecutive pacer cycles and together they present examples where there are normal senses; normal blocked senses; Wenckebach senses; Wenckebach blocked senses; and a PAC. It is to be understood that these examples are illustrative and not limited, and are presented to illustrate how the pacemaker times out each cycle relative to the decision rates that have been determined.

Referring first to FIG. 11a, the top two line diagrams illustrate the scheduled timing of a first cycle, for both atrial and ventricular channels. Referring to the atrial channel, there are three areas shown, namely the tachy area, WB area, and physiologic area. Note that no PVARP is illustrated; in practice, a small PVAB is used, preferably no greater than 10 ms. DWL—int, which separates the tachy and WB area, represents the time (counting from the last atrial event) corresponding to the top rate of the dynamic Wenckebach range. Likewise, DTL—int corresponds to the top rate of the physiologic range, and DPL—int corresponds to the highest rate of the dynamic pacing limit. In this cycle, a Wenckebach sense is indicated, which initiates an AV time out plus AV extension (AVint'), resulting in a VP at a time corresponding to the upper limit of the ventricular physiological rate range. The second sequence of A and V channels is shown to commence with the Wenckebach sense and resulting ventricular stimulus that terminated the first cycle before scheduled time out of DPL—int. This cycle also is interrupted by a Wenckebach sense, and a second (longer) AV extension. A third cycle illustrates a situation where another atrial sense occurs within the Wenckebach area, but sufficiently early such that the maximum AV extension does not permit a physiologic VP. In this situation, the pacemaker schedules a time out of DPL—int from the last VP, i.e., the next VP is at an interval corresponding to the dynamic pacing limit.

Referring to FIG. 11b, there is shown a situation where a PAC occurs, it being noted that it arrives before DWL—int, i.e., before the time corresponding to the top of the WB range. In this situation, it is assumed that no atrial sync pulse can be delivered. As seen in the representation of the second cycle, the atrial tachy area and WB area are timed out before the occurrence of a VP, which happens DPL—int after the VP at the beginning of the first cycle. Shortly thereafter, there is an A sense which is normal in terms of atrial rate, but which is blocked because it occurs so soon after the prior VP that a synchronized VP would exceed ventricular phys—rate. As seen in the illustration of the third set of A and V time diagrams, an A sense occurs in the physiologic area, resulting in a VP following the AV interval. It is interesting to note that in this sequence, there were three A-A intervals, but only two V-V intervals, due to the normal blocked sense.

FIGS. 12a-d illustrate the internal timing and determination of V-A and V-V intervals in terms of the adjusted dynamic pacing interval, DPL—int. It is to be noted that the preferred pacemaker internal timing is ventricular-based, meaning that timers are reset upon the occurrence of a ventricular event, and succeeding atrial and ventricular events are timed out relative to the last ventricular event. However, as illustrated in the timing diagrams, the pacer appears to be based on atrial timing under certain circumstances, namely following a ventricular sense (VS).

Figure 12A:
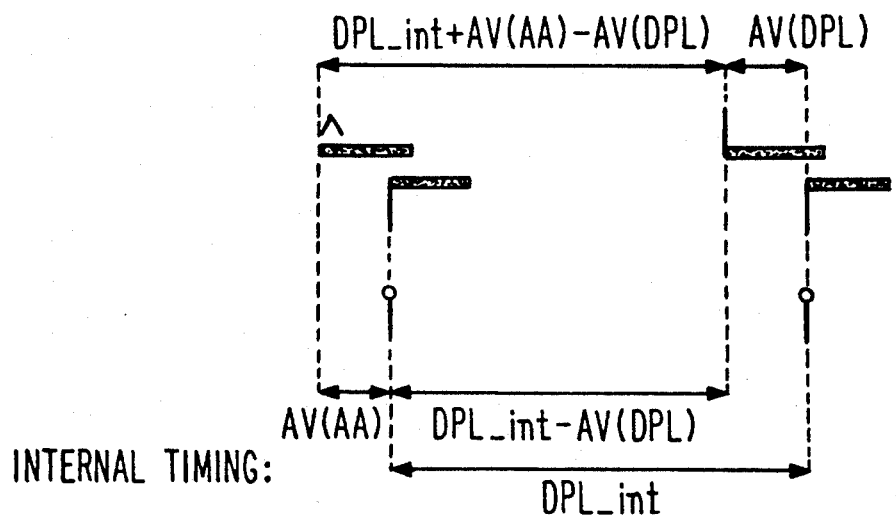
FIGS. 12a–b are timing diagrams that illustrate ventricular based timing examples of the pacemaker of this invention.
Figure 12B:
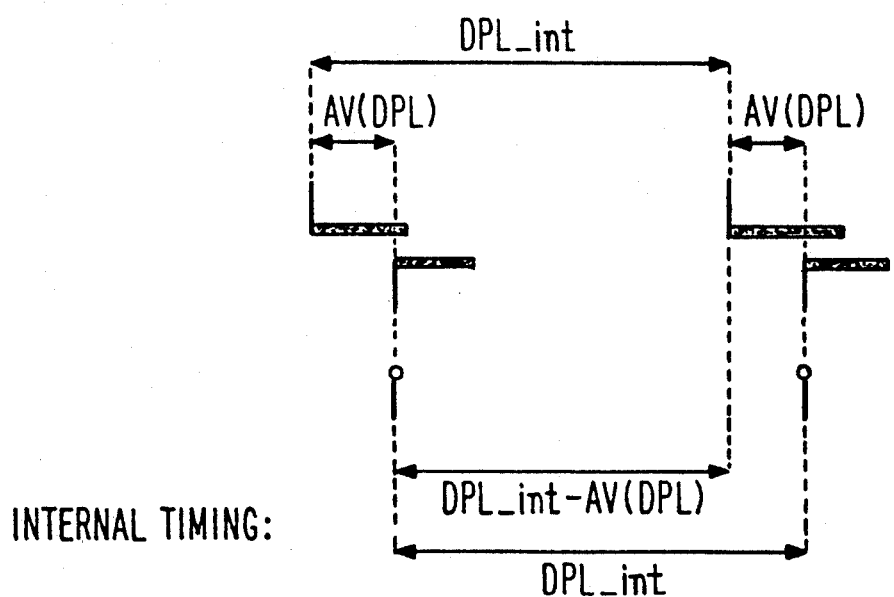

FIGS. 12a and 12b illustrate ventricular-based timing examples. Referring to FIG. 12a, an initial AS is tracked and followed by a VP. The AV interval between AS and VP is set by the pacemaker, and is a function of the atrial timing, i.e., AV(AA). Note the relatively small PVAB. Following the VP, the pacemaker commences to time out the next ventricular cycle, scheduling the next VP after the interval DPL—int. The VA interval is scheduled by subtracting the anticipated AV interval, AV(DPL), from DPL—int. Thus, the resultant AA interval from AS to the anticipated subsequent AP is not DPL—int, but rather DPL—int plus AV(AA) - AV(DPL). It is seen that the atrial interval does not correspond to DPL, but is adjusted to account for the difference between the AV delay following AS (which is a function of the prior AA interval) and the scheduled AV delay following the scheduled AP.

Referring to FIG. 12b, there is shown a second illustration of ventricular-based timing, wherein the first sequence has an AP followed by VP. Under these circumstances, the scheduled AV delay following the next scheduled AP is the same as the last AV delay, such that the A-A interval equals DPL—int. Thus, as expected, where two successive cycles have no sensed event, both atrial and ventricular timing correspond to DPL.

Figure 12C:
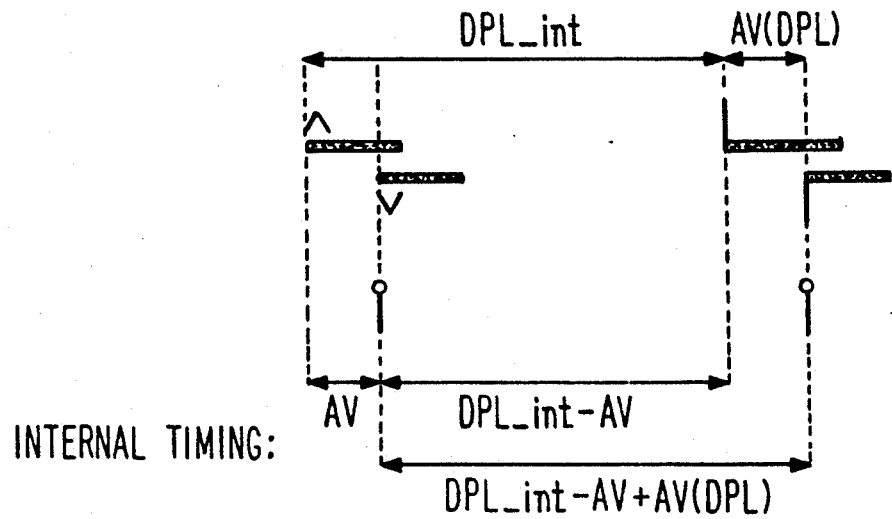
FIGS. 12c–d are timing diagrams that illustrate effective atrial based responses to events.
Figure 12D:
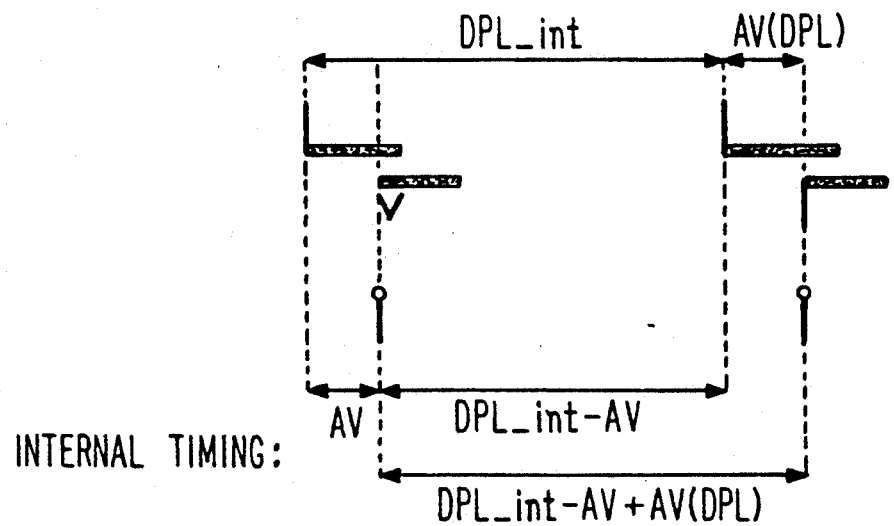

Referring to FIGS. 12c and 12d, there are shown two examples of apparent atrial-based timing, although interval timing is still ventricular based. In FIG. 12c, an AS is followed by a VS, the two being separated by an interval indicated as AV. This AV is shorter than the AV that was scheduled, due to the early AS. Under these circumstances, the pacemaker times out the VA interval by subtracting the last AV interval from DPL—int, so that the scheduled A-A interval equals DPL—int. The next scheduled VP is at AV(DPL) following the scheduled AP, so that the V-V interval equals DPL—int - AV+AV(DPL). FIG. 12d differs from 12c, only in that the initial atrial event is an AP. However, since the atrial event is followed by a VS, the timing is the same. In both of these cases, there is apparent atrial-based timing, since the atrial cycle corresponds to DPL, and the ventricular cycle adjusts to the difference between the adjacent AV intervals.

From the above, it is seen that the pacemaker of this invention is internally ventricular-based, but adjusts its timing depending upon the last AV sequence. Following an early (sensed) ventricular event at phys—rate, atrial timing is maintained in the sense that the scheduled A-A interval is maintained equal to DPL—int, while the next VP is scheduled so as to adjust the difference in timing caused by the early ventricular sense. The next scheduled AP follows the last A event by the dynamic pacing interval if the ventricular event is VS; when the ventricular event is VP, the next ventricular event is set to follow the last ventricular event by DPL—int. Thus, following an early ventricular sense, the shorter AV interval does not affect the scheduled atrial pacing rate, but is made up in lengthening of the ventricular interval. The benefit in this circumstance is that the atrial pacing rate is held steady, instead of being increased in response to an early VS.

Figure 13:
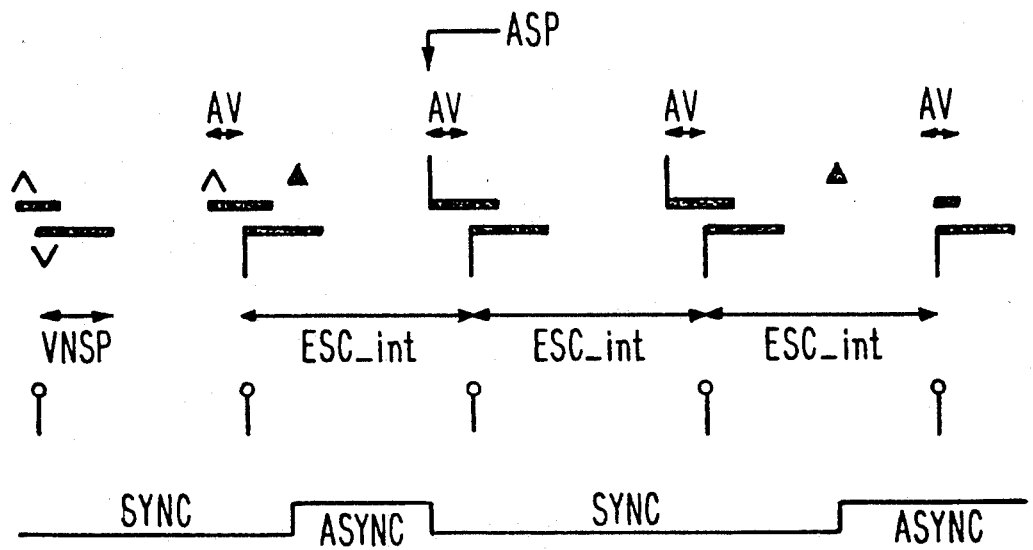
FIG. 13 is a timing diagram illustrating the normal-sync state for DDD mode operation of the pacing system of this invention.

Referring now to FIG. 13, there is shown a timing diagram illustrating the normal sync state for DDD mode. In this state, possible atrial events are NAS, AP and ASP; possible ventricular events are NVS, TVS and VP. The normal sync state is left upon the occurrence upon the following events: for TAS, BAS, NAB, NOA, the system goes to normal async; for WBS, the system goes to WB-sync; and for WBB, the system goes to WB-async. Note that NVES and TVES cause normal async because of the related NOA. TVS causes normal async only if it is preceded by TAS.

In the normal sync state, DDD, the logic is that a NAS starts an AV-delay. If no VS occurs, the ventricle is paced at the end of the timed out AV-delay; and if no AS occurs and the cycle is not yet restarted, the atrium is paced at an AV-delay before the ESC—int. In FIG. 13, there is an example of normal-sync behavior for the DDD mode, where two PAC's are illustrated. Both PAC's cause the normal-async state, but an ASP is introduced after the first PAC to cause a return to normal sync. The ASP is discussed in greater detail below.

Figure 14:
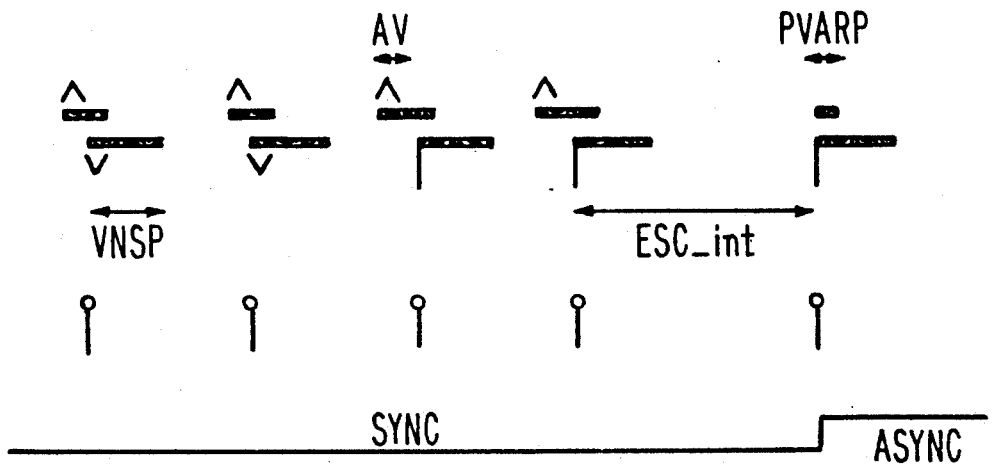
FIG. 14 is a timing diagram illustrating normal-sync state for VDD mode operation of the pacing system of this invention.

Referring to FIG. 14, there is shown a diagram for normal sync state, VDD mode. In this mode, the possible atrial event is NAS; the possible ventricular events are NVS, TVS and VP. The sync state is left in the event of TAS, BAS, NAB and NOA (pacer goes to normal async); WBS (pacer goes to WB-sync); and WBB (pacer goes to WB-async). As with the normal sync state for DDD mode, NVES and TVES cause the pacer to go to normal async because of the related NOA; TVS causes normal async only if it is preceded by TAS. Again, an NAS starts an AV-delay; if no VS occurs, the ventricle is paced at the end of the AV-delay. Note in FIG. 14 that there is an NOA which causes timeout of the full ESC—int, followed by normal async state.

Figure 15A:
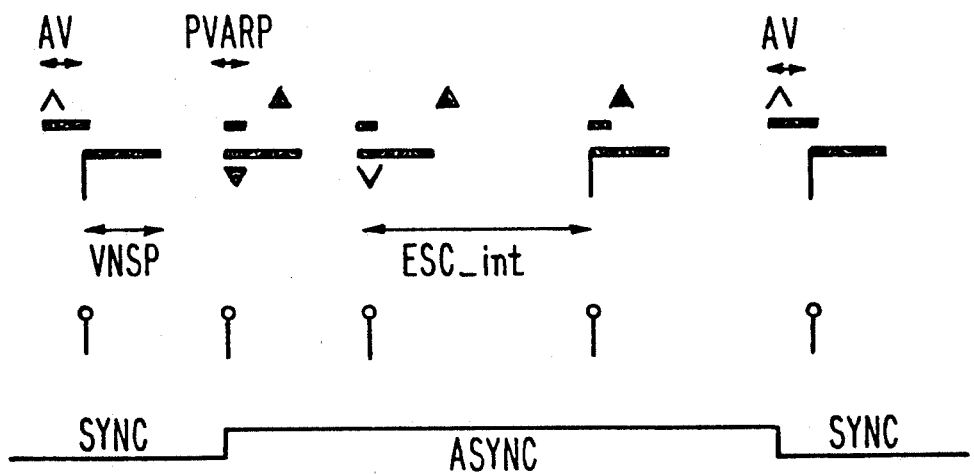
FIGS. 15a and 15b are timing diagrams illustrating normal async state for VDD mode operation of the pacing system of this invention.
Figure 15B:
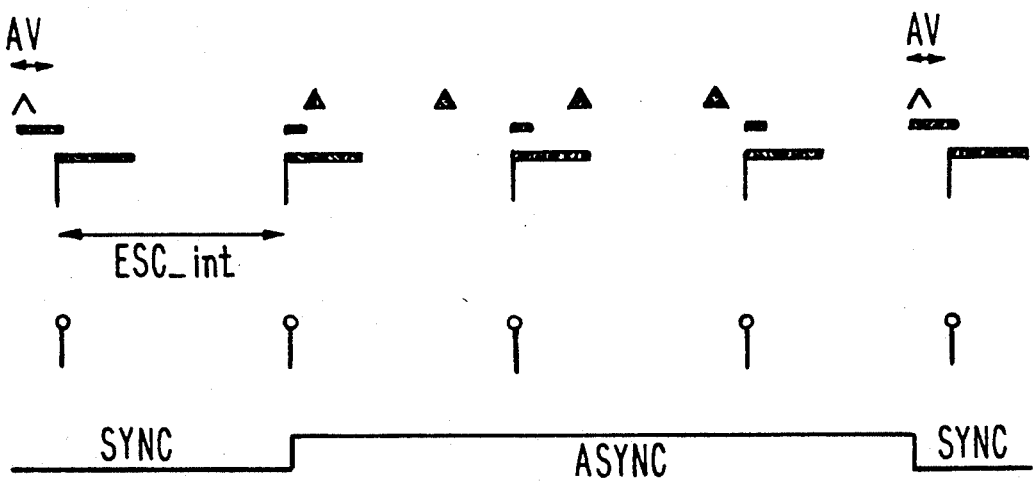

Referring to FIGS. 15a and 15b, there are shown graphs of the normal async state, for VDD and DDD modes. In this state, possible atrial events are TAS, BAS, UAS, NAB and NOA; possible ventricular events are NVS, TVS, NVES, TVES and VP. The normal async state is left in the event of an NAS (to normal sync); AP and ASP (to normal sync, DDD mode only); WBS (to WB sync); and WBB (to WB async). If no VS occurs, the ventricle is paced at the ESC—int. Note in FIG. 15a that there is an extra ventricular systole followed by a TVS. The VES puts the pacemaker into the normal async state, where it remains until an NAS occurs, which returns it to sync. In FIG. 15b, there is an NOA which places the pacer into async, followed by short A-tachy. When an NAS is sensed, the system returns to normal sync.

Figure 16A:
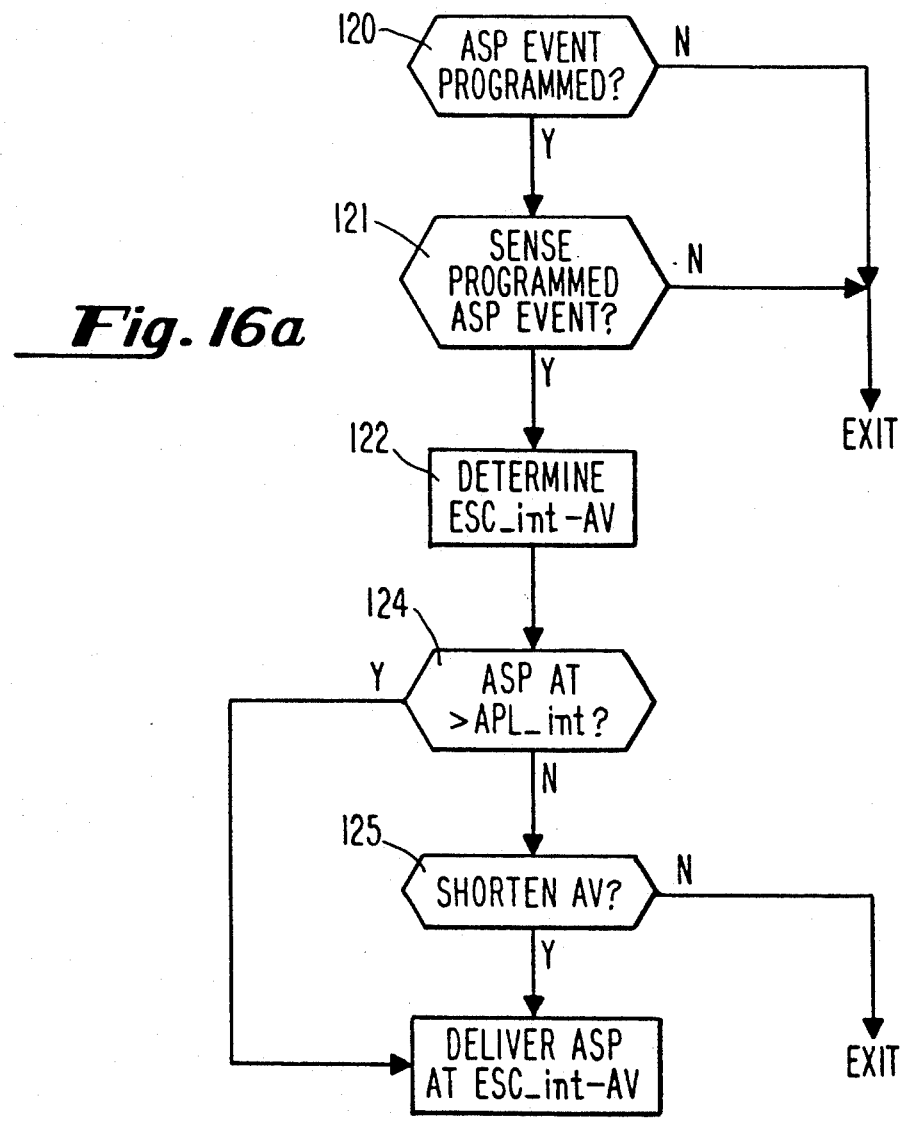
FIG. 16a is a flow diagram of the software steps for determining whether and when an atrial sync pulse (ASP) is delivered in accordance with this invention.
Figure 16B:
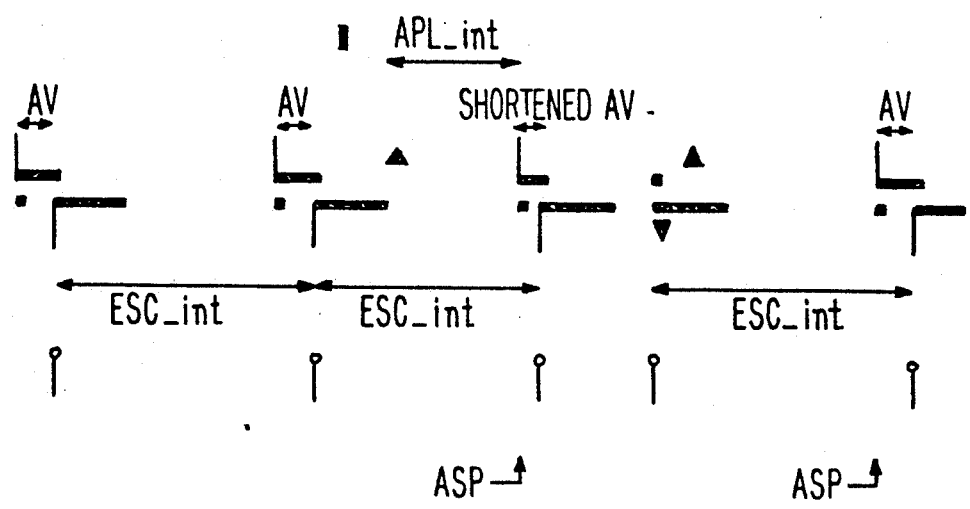
FIG. 16b is a timing diagram illustrating the criteria for delivering an ASP.

The atrial sync pace (ASP) feature is illustrated by FIGS. 16a and 16b. The atrial sync pace is a programmable feature, which can be active in DDI and DDD modes. The ASP feature is utilized to provide safe atrial pacing and to re-synchronize the atrium and the ventricle after certain events, primarily after a PAC or VES. It can also re-synchronize following RC, WBB, BAS, or NAB. The feature is programmable by use of programmer 56, and can be limited to any one or any combination of the above events. The ASP is delivered for the purpose of re-synchronizing following detection of any selected one of the above circumstances, and is generated at an AV-delay before the escape interval. After any one of the above events, or during RC, the software computes the time of escape interval less AV-delay, and determines whether the ASP can be delivered following the timeout of a pre-programmed APL (atrial pace limit) interval, which establishes a minimum safe interval between a prior atrial sense and the ASP pulse. APL—int may be programmed to be the value of DTL—int, UTL—int, UPL—int, or any interval which allows safe atrial pacing without atrial competition. Suitably, AV-delay may be shortened down to a limit of about 6 ms, or any programmable limit. If shortening of the AV-delay still does not permit an ASP to fall prior to expiration of APL—int, then no ASP is delivered.

Referring to FIG. 16a, the pacing system of this invention determines at block 120 whether ASP has been programmed and if so, for which events. If no, the subroutine exits. If yes, the program proceeds to block 121, where it is determined whether a programmed ASP event or condition has been sensed. If yes, the software calculates the ESC—int - AV. Then, at 124, it is determined whether the timed ASP is greater than APL—int, i.e., whether the calculated ASP is to be delivered after timeout of APL. If yes, the program branches to block 126 where the ASP pulse is delivered at the computed time of ESC—int - AV. If no, it is determined at block 125 if AV can be shortened, to any value down to AV-min to allow the ASP. If yes, AV is shortened by the necessary amount. Then, at block 126, the ASP is delivered at the time calculated using the shortened AV interval.

Referring to FIG. 16b, there is shown a timing diagram illustrating the ASP. It is to be noted that the first ASP is caused by a PAC, and the example illustrates AV-delay being shortened so that ASP occurs after timeout of APL—int. The second ASP is caused by an atrial sense preceded by a VES. Note that if the PAC or VES occurs sufficiently after the start of the cycle such that an ASP cannot be delivered except within APL—int, the ASP is suppressed. Thus, the logic provides for delivering a pulse for the purpose of re-synchronizing the heart, but will not permit such an attempt if it would result in too rapid an atrial rate.

Figure 17A:
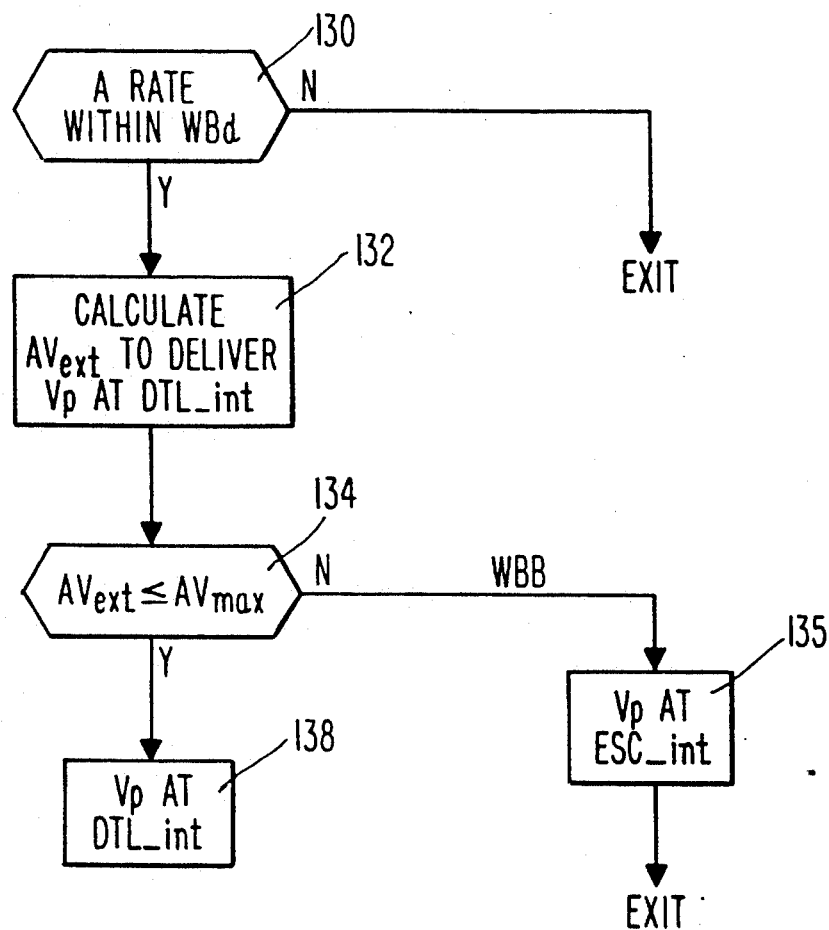
FIG. 17a is a flow diagram of the software steps for Wenckebach operation in accordance with this invention.
Figure 17B:
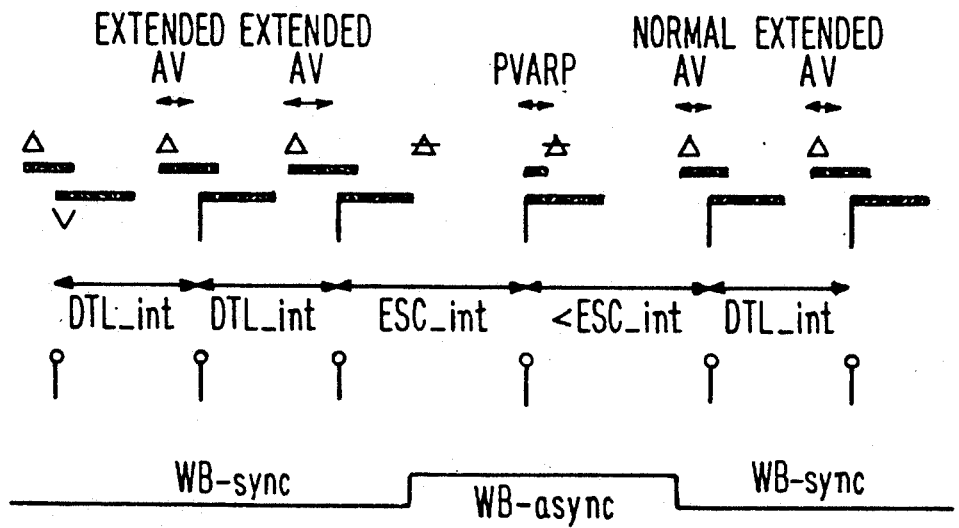
FIG. 17b is a timing diagram illustrating stable Wenckebach behavior in the VDD or DDD mode of operation of the pacing system of this invention.

Referring now to FIGS. 17a and 17b, as well as FIGS. 7a and 7b, there is further illustrated the Wenckebach operation of the pacing system of this invention which provides advantageous differences compared to the conventional prior art Wenckebach modes of operation. As seen in FIG. 17a, the system first checks to determine whether the atrial rate (corresponding to P-P interval) is within the Wenckebach range (corresponding to the Wenckebach distance WBd). If yes, the system calculates what extended AV interval ($AV_{ext}$) is necessary in order to deliver a ventricular pulse at a rate corresponding to the dynamic tracking limit, i.e., at a time corresponding to DTL—int. The value of $AV_{ext}$ is compared to the programmed maximum value, e.g., up to 300 ms, designated $AV_{max}$, at 134. If the extended AV is equal to or less than $AV_{max}$, the atrial event is a WBS, and the software controls the pacemaker to deliver a ventricular pulse which is Wenckebach synced and delivered at DTL—int, as shown at 138. If $AV_{ext}$ is calculated to be greater than the maximum value permitted, the atrial event is interpreted as a WBB, and a ventricular pulse is delivered at the ESC—int, as shown at 135. This is illustrated in the timing diagram in FIG. 17b, where the first three atrial events shown are WBS events; the result of the WBS event is that the extended AV is determined, and a ventricular stimulus is delivered following timeout of DTL—int, corresponding to the highest tracking rate. As long as this condition prevails, tracking is in a WB-sync state. The fourth atrial sense is a WBB, caused by the prior extended AV-delays. This puts the pacer into WB-async state, where pacing of the ventricle is at ESC—int (corresponding to DPL); after two such WBB the system re-synchronizes to WB-sync. The pacer may also go from WB-sync to WB-async on the occurrence of a BAS or NOA. It will return to normal sync upon the occurrence of an NAS, or an AP (DDD mode only); and will go to normal async upon the occurrence of a TAS or NAB. A TVS will only cause normal async if it is preceded by a TAS.

It is to be noted that the AV interval is generally a function of atrial rate for the pacing system of this invention. Thus, in WB operation as well, the AV interval before extension is a function of atrial rate. The extension can be limited as stated above, so that the entire extended AV interval is subject to a limit; or preferably the amount of AV extension alone can be limited to a programmed value. Either of these arrangements is within the scope of the invention. The result of the improved Wenckebach arrangement of this invention is that no atrial sense is blocked, as is done in conventional Wenckebach operation. Thus, in the prior Wenckebach pacer, the AV extension causes a block every n beats. With this arrangement, if the AV cannot be extended, there is no synchronous pulse delivered, but rather the ventricle is paced at the ESC—int. This results in an average V stimulus rate which is dropped below DTL, but provides a steadier beat than in prior art Wenckebach modes, because no ventricular pulse is missed due to blocking. Most atrial beats in the Wenckebach range are well synchronized, for the case where $AV_{ext}$ is less than or equal to $AV_{max}$, and the sudden drop of the ventricular pulse rate due to block is avoided. Note also that in the prior art Wenckebach mode, anytime an atrial sense is within the Wenckebach window, a ventricular sync pulse is given, no matter how high the atrial rate might be. Such a high rate can be caused, in the prior art, because an intermediate A sense may have been missed due to falling in the refractory interval. In the pacemaker of this invention, PVARP is made very small, to minimize the occasions when atrial senses are blanked and to insure substantially continuous sensing of natural atrial events. Indeed, PVARP is preferably simply PVAB, as discussed above. Additionally, as discussed above in connection with FIG. 7b, in the fixed Wenckebach mode of this invention the pacemaker can get to Wenckebach only by a physiological path. This result is achieved by limiting the upward jump in the phys_rate, e.g. to 2 ppm/cycle. This constrains the pacemaker to proceed virtually to UTL before the Wenckebach range can be reached, i.e., the WB range can be reached only when DTL reaches UTL. By this means, a sudden non-physiological rate change cannot result in the Wenckebach state.

Figure 18A:
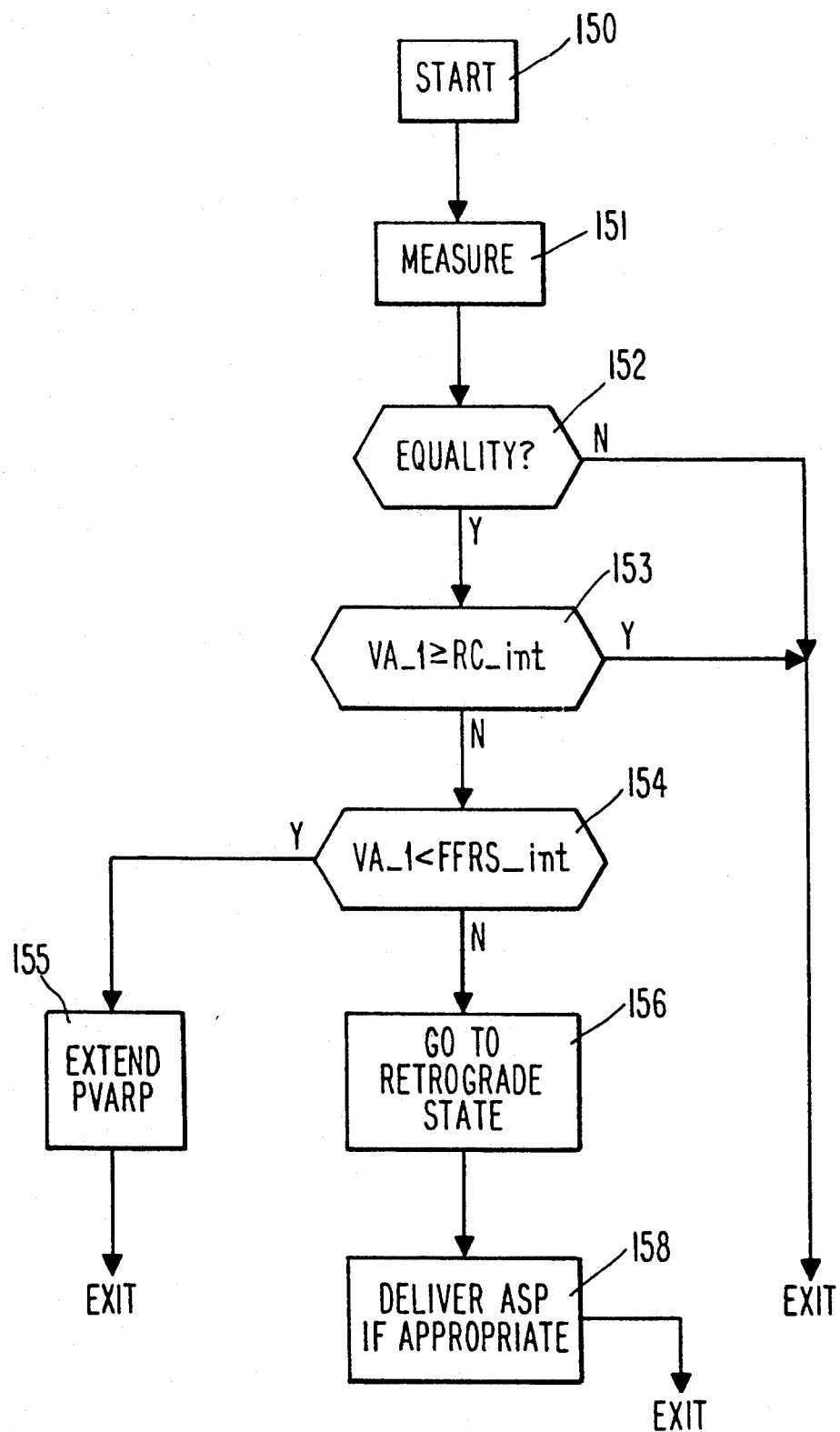
FIG. 18a is a flow diagram representing the VA conduction test of this invention.
Figure 18B:
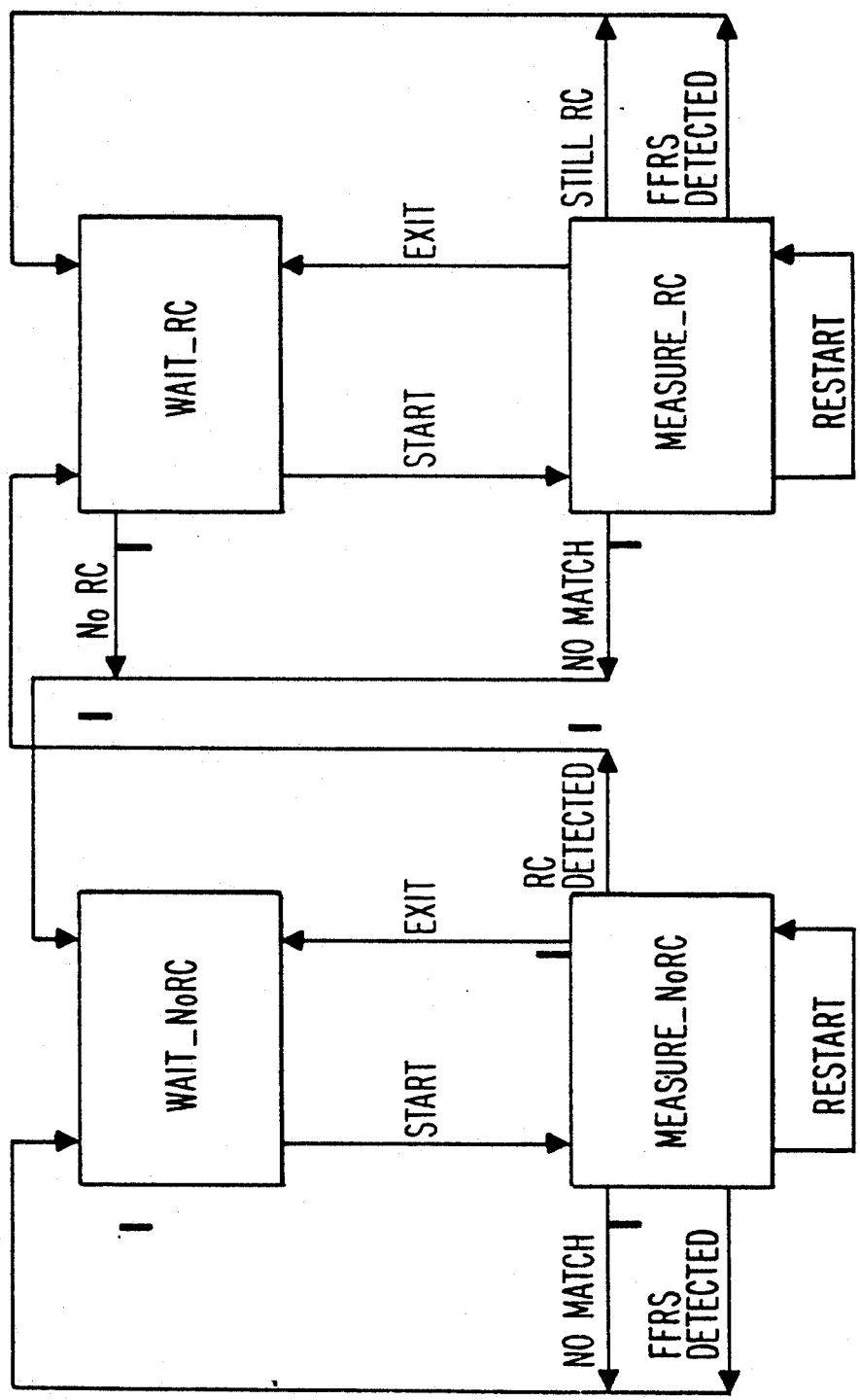
FIG. 18b is a state diagram illustrating the VA conduction test.

Referring now to FIGS. 18a and 18b, there is illustrated the means by which the pacemaker of this invention searches for and determines retrograde conduction (RC), and also determines whether there is far field R-wave sensing (FFRS). The VA conduction detection test detects the presence and absence of both RC and FFRS by periodically changing the AV_interval (in the synchronous state) or the VV_interval (in the asynchronous state), and monitoring to see if the VA_interval remains constant. If the interval does remain constant, this raises a suspicion of retrograde conduction. The second criterion is that the VA interval is between a programmable RC-criterion (e.g., 300 or 450 ms) and programmable FFRS-criterion (e.g., 150 ms). Likewise, FFRS is suspected if the substantially constant VA_interval is below the FFRS-criterion (e.g., less than 150 ms). If RC is detected, the pacer goes into a retrograde state, which is an asynchronous state (e.g., VVIR, DDIR) in which atrial senses are ignored and are not tracked to the ventricle, thus preventing or terminating PMT's. If FFRS is determined, the PVARP is extended to a duration just beyond the detected FFRS-time. This extended PVARP suppresses the far field R-wave sensing, but with a PVARP calculated to be as small as possible. The pacemaker reverts PVARP to its original value after a programmed period of days.

As used in this invention, the monitoring of the VA_int can be done by directly measuring VA time, but can also be done by sensing AA time. Thus, since AA time tracks VA time very closely, then variations of AA time can also represent a measure of VA time. Thus, as used in claiming this invention, a measure of VA conduction interval may be either the precise VA interval time, or may be, for example, AA interval time.

While a first embodiment for differentiating between FFRS and RC is that of comparing the substantially constant VA_int to a predetermined interval, the invention embraces an alternate embodiment for differentiating between RC and FFRS. In the alternate embodiment, during the test the pacemaker looks for and determines the number of A senses per cycle over a test of N cycles (N can vary, for example, from 1 to 100). It is known that during retrograde conduction, there would be only one atrial sense per cycle. However, during FFRS, there would probably be two atrial senses per cycle. Thus, the pacemaker algorithm compares the measured number of A senses per cycle to the predetermined value (r) of atrial senses per cycle, where r can be anything between 1 and 2. If the detected number of A senses per cycle is greater than r, then FFRS is indicated, or diagnosed; if less than r, then RC is indicated.

It is to be noted that VA conduction detection can be executed in all states, and not just in the atrial sync or normal atrial state. While in the RC state, the pacer delivers an ASP if conditions warrant, to attempt to re-synchronize. Once the end of retrograde conduction has been detected, the system goes to the normal async state, from where it can return to normal sync or other states. In summary, the pacemaker can go to retrograde state from normal sync; normal async; Wenckebach sync and Wenckebach async. At the determination of end of retrograde conduction, the pacemaker returns from retrograde state to normal async.

Referring now to FIG. 18a, there is shown a flow diagram which represents the main steps of the software for entering the retrograde conduction test, and responding to the test. As indicated at 150, the retrograde conduction test is started, upon the detection of events that indicate the possibility of an undesirable VA conduction. The criteria for starting are variable, but preferably include detection of a certain number of successive ventricular pulses with a corresponding high percentage following atrial senses, e.g., at least 80% atrial sensing during 32 consecutive VP. When and if start is initiated, the measurement of VA conduction time is performed at 151, over a predetermined number of cycles. This includes the steps set forth above, of changing AV or VV interval, and measuring VA interval. Then, at 152, it is determined whether there is VA equality, i.e., is VA time substantially equal?. The criteria for determining equality are programmable, but generally require a predetermined minimum deviation in the VA interval over a predetermined number of successive VA measurements. If there is no equality found, the software exits the subroutine. If equality is found, software goes to block 153, where it is determined whether the first VA interval (VA_1) is equal to or greater than the RC interval (RC_int), the $RC_{13}$ interval representing a programmed value below which retrograde conduction may be defined. If this VA interval is larger than the RC_interval criteria, then the subroutine exits. If not, it then determines whether the VA_interval is less than FFRS_interval, as illustrated at 154. If yes, meaning that far field r wave sensing has occurred, PVARP is extended to equal the VA_interval plus a predetermined programmable safety margin, as indicated at 155. If no, then the logic requires that VA_1 is between the RC and FFRS criteria, such that retrograde conduction has been determined. The software then goes to retrograde state, as indicated at 156. During retrograde state, an ASP is delivered, if the criteria as discussed above are met, as indicated at 158.

The flow diagram of FIG. 18A is modified where the alternate embodiment for differentiating between RC and FFRS is utilized. In this alternate embodiment, the measuring step at 151 also includes accumulating the number of atrial senses per cycle. When and if equality is determined at block 152, steps 153 and 154 are replaced with the single step of comparing the measured rate of atrial senses per cycle with the predetermined value r. It is further noted that the second differentiating step can be used as a redundant step, whereby differentiation is found both when the VA interval is found to be less than the FFRS_interval, and when the atrial sense rate criterion is met.

Referring now to FIG. 18b, there is shown a state event diagram for carrying out the VA conduction test. VA conduction detection consists of the following four VA-states:

Wait_NoRC
Wait_RC
Measure_NoRC
Measure_RC

In Wait_NoRC, the system waits until there is an indication that VA conduction is possible; in Wait_RC, the system waits until either the occurrence of predetermined heart events that indicate the end of RC, or a programmed wait time has expired to initiate re-checking the presence of RC. In both measure states (Measure_NoRC and Measure_RC), this system shall:

change the AV_interval (sync-states) or the VV_interval (async-states);
measure three VA_intervals;
check if these are constant; and
decide if there is RC, FFRS or no VA conduction.

In the measurement procedure of the RC conduction detection, the following definitions apply:

(a) VA_1, VA_2, VA_3:
measured VA_interval in three successive cycles;
(b) Equality: the three measured VA_intervals are equal within a certain accuracy:
|VA_1- VA_2| < Stability_criterion (programmable in ms); and
|VA_1- VA_3 < Stability_criterion
(c) Start: the events indicate the possibility of VA conduction:
There are 32 successive VP with at least 26 AS (i.e. ≧80% atrial sensing; VES are discarded);
(d) Restart: a second or third check is needed to confirm RC or FFRS:
There is Equality;
Equality has not yet occurred three successive times;
(e) RC Detected:
Equality is found three successive times; and
FFRS_criterion ≦ VA_1 < RC_criterion;
(f) FFRS Detected:
Equality is found three successive times; and
VA_1 < FFRS-criterion;
(g) Exit: the events indicate the probable absence of VA conduction:
There is a VS, AP, ASP or NOA;
(h) No RC: the events indicate the absence of VA conduction:
There are three successive cycles with VS and/or AP, ASP, NOA;
(i) No Match: there is no VA conduction, because the measured VA_intervals are unequal or too long:
There is no Equality; or
VA_1 ≧ RC_criterion;
(j) Still RC: RC is found again while the system is in the Retrograde state:
Equality is found once (there is no need for a second or third check); and
FFRS_criterion ≦ VA_1 < RC_criterion.

The procedure used in both Measure_NoRC and Measure_RC states is as follows:
(a) This state shall take a maximum of 5 cycles;
(b) Cycle 1:
Keep the pacing rate constant ("Freeze" DPL)
Measure VA_1
in sync-states: extend the AV delay with VA_delta (a programmable value, e.g., 50 ms);
in async states: extend the Esc_int with VA_delta;
(c) Cycle 2:
Keep the pacing rate constant ("Freeze" DPL);
Measure VA_2
(d) Cycle 3:
Measure VA_3
(e) Cycle 4, Cycle 5:
Wait
(f) Upon the occurrence of one of the following events, Measure_RC and Measure_NoRC are terminated in any of the 5 cycles:
Exit
No Match
RC Detected
FFRS Detected
Still RC (only in Measure_RC)
(g) Restart occurs automatically after cycle 5, i.e., the 5 cycle measurement procedure is repeated.

As noted in the above definitions, detection of RC requires equality to be found three successive times (as a result of three successive 5-cycle measurements) and the VA conduction time to be between the prescribed RC and FFRS criteria; and FFRS is detected when equality is found three successive times, and the VA conduction time is less than the FFRS criterion.

It is seen from the above description that there is provided a combined retrograde conduction and far field R wave sensing test which provides improved scope for detecting these two conditions. The test is operable in either the sync or async mode, and is not limited to high atrial rate or tachy atrial rate conditions for defining PMT. The one VA time measurement test is utilized both for detecting RC and FFRS.

What is claimed:

1. A dual chamber pacemaker system, having ventricular stimulus means for generating and delivering pacing pulses to the patient's ventricle, atrial sensing means for sensing atrial signals from the patient's atrium, means for determining a measure of atrial rate form said atrial signals, and ventricular sensing means for sensing ventricular signals from the patient's ventricle, further comprising:

means for determining a physiological rate as a function of atrial rate, whereby said physiological rate tracks the rate of sensed physiological atrial signals;
range means for defining a physiological range of atrial rates relative to and varying with said physiological rate;
AV means for timing out an AV delay; and
sync means for enabling time out of an AV delay for synchronizing delivery of ventricular pacing pulses with respect to atrial heartbeats which occur within said physiological range, said ventricular pacing means being operatively controlled by said sync means to deliver a pacing pulse following time out of a said AV delay.

2. The pacemaker system as described in claim 1, further comprising sensor means for determining desired pacing rate, and atrial stimulus means controlled by said sensor means for generating and delivering atrial stimulus pulses to the patient's atrium when the determined pacing rate overtakes the patient's natural atrial rate, and wherein said physiological rate means comprises means to change said physiological rate to be substantially said pacing rate when said pacing rate overtakes said natural atrial rate.

3. The pacemaker system as described in claim 1, wherein said range means comprises means for defining a dynamic tracking limit at the top of said physiological range and a dynamic pacing limit at the bottom of said physiological pacing limit defining said range, and means for coupling changes in said limits to changes in said physiological rate over at least a predetermined range of physiological rates.

4. The pacemaker system as described in claim 3, wherein said range means comprises limit means for limiting changes in said dynamic tracking limit to an upper tracking limit and a lower tracking limit.

5. The pacemaker system as described in claim 3, comprising means for limiting said dynamic pacing limit by an upper pacing limit and a lower pacing limit.

6. The pacemaker system as described in claim 1, comprising means for determining the VV interval of successive ventricular events, means for determining when said VV interval is within said physiological range, and means for enabling AV sync only when the resulting VV interval is within said physiological range.

7. The pacemaker system as described in claim 6, comprising extension means for extending AV time out to a predetermined maximum AV extension.

8. The pacemaker system as described in claim 1, comprising Wenckebach means for defining Wenckebach range and for setting said dynamic Wenckebach range relative to said physiological rate, whereby said dynamic Wenckebach range is coupled to said physiological rate.

9. The pacemaker system as described in claim 1, wherein said range means comprises means for tracking said physiological range linearly with said physiological rate within a predetermined range of physiological rates.

10. The pacemaker system as described in claim 1, wherein said system operates cyclically, and comprising means for determining said physiological rate each cycle of said system, and means for setting said Wenckebach range relative to said determined physiological rate each said cycle.

11. The pacemaker system as described in claim 1, comprising ASP means for delivering an atrial sync pulse (ASP) following an atrial sense having a rate greater than said physiological range.

12. A dual chamber pacemaker system, having stimulus means for stimulating at least in the ventricle and for sensing in both the atrium and the ventricle, and sync means for timing out an AV delay following sensing of an atrial signal, comprising
rate means for continuously determining the atrial rate of atrial events and physiological means for continuously determining from said atrial rate a physiological rate;
dynamic range means for defining a dynamic rate range relative to said physiological rate;
VV means for determining the rate of a ventricular stimulus to be delivered at the time out of said AV delay;
means for determining when the atrial rate of said sensed atrial signal is within said dynamic range and when the delivered ventricular stimulus is at a ventricular rate within said dynamic range and
AV sync enabling means for enabling said stimulus means to deliver a ventricular stimulus at the time out of said AV delay only when said atrial rate and said ventricular rate are within said dynamic range.

13. The pacemaker system as described in claim 12, wherein said sync means comprises means for setting said AV delay as a function of atrial rate.

14. The pacemaker system as described in claim 12, wherein said dynamic range means comprises means for varying said dynamic range with physiological rate within predetermined upper and lower range limits, and means for limiting said range to a predetermined range of bpm regardless of said physiological rate.

15. The pacemaker system as described in claim 12, comprising means for setting the escape interval of said stimulating means to equal a predetermined lower limit of said dynamic range.

16. The pacemaker system as described in claim 12, comprising Wenckebach range means for determining a dynamic Wenckebach range above the upper limit of said dynamic range, and Wenckebach sync means for delivering Wenckebach ventricular sync pulses following atrial signals in said dynamic Wenckebach range.

17. The pacemaker system as described in claim 12, further comprising means for stimulating the patient's atrium at a rate corresponding to the lower limit of said dynamic rate range, and wherein said rate means comprises means for changing said physiological rate toward said atrial pacing rate when the atrium is paced.

18. The pacemaker system as described in claim 12, wherein said pacemaker system operates cyclically, and said rate means comprises means for adjusting said physiological rate each pacemaker cycle as a function of said determined atrial rate.

19. The pacemaker system as described in claim 18, wherein said rate means comprises means for adjusting said physiological rate toward the determined atrial rate by a predetermined increment following each physiological atrial event.

20. The pacemaker system as described in claim 12, further comprising sensor means for developing a sensor-indicated pacing rate, and dynamic pacing limit means for limiting the lower limit of said range to the sensor indicated pacing rate.

21. The pacemaker system as described in claim 20, comprising means for adjusting said physiological rate to match said sensor-indicated pacing rate when said sensor-indicated pacing rate overtakes the patient's atrial rate.

22. A dual chamber pacemaker system, having ventricular generating means for generating and delivering stimulus pulses to a patient's ventricle, atrial sensing means for sensing atrial signals from the patient's atrium, and synchronous means for controlling the ventricular generating means to deliver ventricular stimulus pulses synchronized to preceding sensed atrial events, characterized by:
storing means for storing atrial event parameter data defining physiological atrial events, said stored data including rate data;
atrial event means for determining parameter data associated with sensed atrial signals;
comparing means for comparing the determined atrial event data with said stored data to determine if the atrial event is physiological, and data adjusting means for adjusting said stored data as a function of at least the rate of each physiological atrial event; and
control means for controlling said synchronous means to deliver a synchronized ventricular stimulus pulse only when a preceding atrial event is determined to be physiological.

23. The pacemaker system as described in claim 22, further comprising means for determining the rate of a ventricular stimulus synchronized pulse to follow a sensed atrial event, and for comparing said rate to said physiological data to determine if said synchronous pulse is physiologic; and controlling means comprising means for limiting the generation of synchronous ventricular pulses to those which are determined to be physiologic.

24. The pacemaker system as described in claim 23, wherein said storing means comprises means for storing data defining an atrial rate range, and further comprising means for determining the rate of each atrial event, and wherein said comparing means further comprises means for determining that an atrial event is physiologic only when the rate of said atrial event is within said atrial rate range.

25. The pacemaker system as described in claim 22, wherein said data adjusting means comprises rate means for determining a physiological rate as a function of the rate of atrial events, and further comprising range means for determining a physiological rae range coupled to said physiological rate, said control means controlling said synchronous means to deliver a synchronous ventricular pacing pulse only following atrial events determined to be within said physiological rate range.

26. The pacemaker system as described in claim 25, further comprising Wenckebach means for defining a Wenckebach range having a predetermined relation to said rate range, and Wenckebach control means for controlling said ventricular generating means to deliver ventricular stimulus pulses in a Wenckebach relation to atrial events having rates falling in said Wenckebach range.

27. A dual chamber pacemaker system, having ventricular generating means for generating and delivering stimulus pulses to a patient's ventricle, atrial sensing means for sensing atrial signals from the patient's atrium, and rate means for determining the atrial rate of a sensed atrial signal, further comprising:

(a) physiological range means for setting a physiological rate of rates, and means for determining whether a said atrial rate is within said physiological rate range;

(b) physiological rate means for determining a physiological rate as a function of said atrial rate following a determination that said atrial rate is within said physiological range;

(c) said physiological range means including range adjusting means for adjusting said physiological range relative to and varying with said physiological rate;

(d) means for determining the timing of a ventricular stimulus to be synchronized with a sensed atrial signal that has been determined in step (a) to be at a rate within said physiological range;

(e) means for determining if said synchronized ventricular stimulus is within said adjusted physiologic range; and (f) synchronous means for pacing the patient's ventricle with said synchronous ventricular stimulus when its rate is determined to be within said adjusted physiological range.

28. The pacemaker system as described in claim 27, wherein said range adjusting means comprises lower limit means for determining a dynamic pacing limit (DPL) having a rate below said physiological rate and wherein said lower limit means tracks said DPL relative to said physiological rate, said DPL establishing the lower limit of said physiological range.

29. The pacemaker system as described in claim 27, wherein said range adjusting means further comprises an upper limit means for determining a dynamic tracking limit (DTL) at a rate above said physiological rate, and said DTL being the upper limit of said physiological range, and wherein said upper limit means tracks said DTL at a predetermined rate above said physiological rate.

30. The pacemaker system as described in claim 29, comprising pacing control means for controlling said ventricular generating means to deliver a stimulus pulse at an escape interval corresponding to said DPL when either said sensed atrial signal or said determined synchronous ventricular stimulus is outside of said physiological range.

31. The pacemaker system as described in claim 30, comprising ASP means for delivering an atrial pulse (ASP) to the patient's atrium following sensing of an atrial signal outside of said physiological range, said ASP means including control means for controlling delivery of an ASP subject to the condition that the synchronous ventricular rate corresponding to said ASP is within said physiological range.

32. The pacemaker system as described in claim 29, comprising Wenckebach means for defining a Wenckebach rate range above said DTL, and Wenckebach control means for controlling said ventricular stimulus generator to generate a ventricular stimulus pulse in a Wenckebach relation following sensing of an atrial signal within said Wenckebach range.

33. The pacemaker system as described in claim 27, comprising asynchronous means for controlling said ventricular generating means to generate a stimulus pulse which is asynchronous relative to said sensed atrial signal when said atrial signal is outside of said physiological range, having means to control said ventricular stimulus generator to generate a ventricular stimulus synchronized to the next sensed atrial signal which is determined to be within said physiological range.

34. The pacemaker system as described in claim 27, further comprising rate responsive sensor means for determining a sensor-indicated pacing rate, and said range adjusting means having coupling means for coupling said physiological range to said sensor-indicated rate when said sensor indicated rate overtakes atrial rate.

35. The pacemaker system as described in claim 34, wherein said physiological means comprises means for determining the physiological rate as a function of atrial and said sensor-indicated rate.

36. A dual chamber pacemaker system, having ventricular stimulus means for generating and delivering stimulus pulses to the patient's ventricle, and ventricular sensing means for sensing ventricular signals from the patient's ventricle, and atrial sensing means for sensing atrial signals from said patient's atrium, comprising:

(a) tracking range means for determining a variable upper atrial rate tracking limit (DTL) and a lower rate atrial rate tracking limit (DPL), the range between said DTL and said DPL defining a tracking range;

(b) means for determining the rate of said sensed atrial signals and for determining whether each said atrial rate is within said tracking range;

(c) means for varying said DTL as a function of atrial rate for atrial rates determined to be within said tracking range; and (d) ventricular control means for controlling said ventricular stimulus means to pace the ventricle in synchronous relation to a sensed atrial signal only when the atrial rate is within said range.

37. The pacemaker system as described in claim 36, wherein said ventricular control means comprises timing means for determining the timing of a said ventricular stimulus to be delivered, and prevent means for preventing delivery of a synchronous ventricular stimulus unless the rate of said timed synchronous stimulus is within said tracking range.

38. The pacemaker system as described in claim 37, wherein said ventricular control means comprises AV means for timing out a predetermined AV delay and for extending said AV delay following a sensed atrial signal up to a predetermined extension limit in order to generate a synchronous ventricular pulse at a ventricular rate within said tracking range.

39. The pacemaker system as described in claim 36, wherein said varying means further comprises physiological rate means for determining a physiological rate as a function of atrial rates determined to be within said tracking range, and set means for setting said DTL and said DPL and said DPL relative to said physiological rate.

40. The pacemaker system as described in claim 39, wherein said physiological rate means comprises atrial rate change means for determining whether an atrial rate has changed by more than a predetermined amount, said physiological rate means having adjust means for adjusting said physiological rate as a function only of atrial rates determined to have changes within said rate change limit.

41. The pacemaker system as described in claim 39, further comprising sensor means for determining a sensor-indicated rate from at least one patient parameter, and wherein said physiological rate means comprises adjust means for adjusting said physiological rate as a function of said atrial rates and said sensor-indicated rates.

42. The pacemaker system as described in claim 39, wherein said tracking range means comprises maintaining means for maintaining said DPL below said physiological rate while natural atrial beats are sensed.

43. The pacemaker system as described in claim 39, wherein said tracking range means comprises varying means for varying said range linearly with respect to said physiological rate over a predetermined range of physiological rates.

44. The pacemaker system as described in claim 36, further comprising sensor means for determining a sensor-indicated rate, and wherein said tracking means comprises sensor control means for controlling at least said DPL as a function of said sensor-indicated rate.

45. The pacemaker system as described in claim 36, comprising Wenckebach range means for defining a Wenckebach range above said rate range, and Wenckebach control means for controlling said ventricular stimulus means to pace the ventricle according to a Wenckebach response following sensing of an atrial event in said Wenckebach range.

46. A dual chamber pacing system having atrial sense means for sensing atrial events, tracking means for tracking sensed atrial events, ventricular stimulus means for delivering ventricular pulses, and synchronous means for controlling said ventricular stimulus means to deliver ventricular pacing pulses in synchronous relation to tracked atrial events said tracking means comprising:

upper limit means for setting an upper atrial tracking limit above which atrial events are not tracked for synchronizing ventricular pulses;

atrial rate means for determining the rates of sensed atrial events that occur at a rate below said upper tracking limit; and adjusting means for adjusting said upper tracking limit as a function of said atrial rates.

47. The dual chamber pacing system as described in claim 46, wherein said synchronous means comprises means for timing out an AV delay following a sensed atrial signal, rate determining means for determining the rate of delivery of a synchronous pulse delivered at said AV delay following a sensed atrial signal, and prevent means for preventing delivery of a synchronous pulse where said determined synchronous rate is greater than said upper limit.

48. The dual chamber pacing system as described in claim 46, wherein said atrial sense means comprises an atrial sense circuit having means for sensing continuously each pacer cycle.

49. A method of scheduling atrial and ventricular pace events in a dual chamber pacemaker, said pacemaker having means for sensing atrial signals (AS) and ventricular signals (VS), means for delivering atrial pace pulses (AP) and ventricular pace pulses (VP), and means for determining the AV interval between an atrial event and a following (VS), comprising:

determining an escape interval for delivering pace pulses, and delivering APs and VPs in the absence of natural atrial and ventricular signals;

following each VS, scheduling the next AP to follow said VS by said escape interval minus the determined AV interval which was terminated by said VS, whereby the next scheduled A—A interval equals said escape interval; and following each VP, scheduling the next VP to follow said VP by said escape interval.

50. The dual chamber pacing system as described in claim 49, wherein said escape interval is a dynamic pacing limit (DPL) interval, and comprising determining physiological atrial senses and the rate of said physiological atrial senses, and determining said pacing limit interval as a function of the rate of physiological atrial senses.

51. The dual chamber pacing system as described in claim 49, comprising determining, following each AS, a scheduled AV interval as a function of said physiological atrial rate.

52. The dual chamber pacing system as described in claim 50, comprising determining, after an AP, a scheduled AV interval as a function of DPL.

53. The dual chamber pacing system having atrial sense means for sensing atrial events, tracking means for tracking sensed atrial events, ventricular stimulus means for delivering ventricular pulses, decision means for determining when sensed atrial events are and are not to be tracked, and synchronous means for controlling said ventricular stimulus means to deliver ventricular pacing pulses in synchronous relation to atrial events determined to be tracked, said pacing system further comprising:

atrial sync pulse (ASP) means for delivering an ASP to a patient's atrium following sensing of an atrial signal which is determined not to be tracked, said ASP means having scheduling means for scheduling delivery of said ASP at least a predetermined interval following the non-tracked atrial signal; enabling means for enabling said ASP means; and program means for programming and storing a plurality of selectable conditions under which said ASP means is enabled to deliver an ASP.

54. The pacing system as described in claim 53, comprising means for detecting an atrial signal which is Wenckebach blocked, and wherein said program means comprises means for programming said ASP means to be enabled following detection of an atrial signal which is Wenckebach blocked.

55. The pacing system as described in claim 53, comprising means for detecting retrograde conduction, and wherein said program means comprises means for programming said ASP means to be enabled following detection of retrograde conduction.

56. The dual chamber pacemaker system, having ventricular generating means for generating and delivering stimulus pulses to a patient's ventricle, atrial sensing means for sensing atrial signals from the patient's atrium, and synchronous means for controlling the ventricular generating means to deliver stimulus pulses synchronized to selected preceding sensed atrial events, characterized by:

said synchronous means having decision rate means for selecting said selected preceding atrial events as a function of the rate of said preceding sensed atrial events, and said atrial sensing means having limited blocking means for blocking sensing of atrial events for only a limited time following each ventricular pulse, thereby blocking sensing of far field R waves.

57. The pacemaker system as described in claim 56, wherein said limited blocking means comprises means for blocking sensing of atrial events for a time duration of no more than 10 ms following delivery of a ventricular stimulus pulse.

58. The dual chamber pacemaker system as described in claim 56, wherein said limited blocking means comprises means for providing a programmable time period following a ventricular stimulus for blocking sensing, means for detecting the condition of sensing far field R waves and means for extending said programmable time period only when said condition is detected.

* * * * *